(12) United States Patent
Shattuck et al.

(10) Patent No.: US 12,048,429 B2
(45) Date of Patent: Jul. 30, 2024

(54) VESSEL CLOSURE DEVICES AND METHODS

(71) Applicant: NeuroFine Corp., Miramar, FL (US)

(72) Inventors: Nicholas Shattuck, Lauderhill, FL (US); Brad D. Aurilia, Coral Springs, FL (US); Quinton Wiebe, Davie, FL (US); Daniel Sablyak, Sunrise, FL (US)

(73) Assignee: NeuroFine Corp., Miramar, FL (US)

( * ) Notice: Subject to any disclaimer, the term of this patent is extended or adjusted under 35 U.S.C. 154(b) by 29 days.

(21) Appl. No.: 17/546,958

(22) Filed: Dec. 9, 2021

(65) Prior Publication Data
US 2022/0183677 A1    Jun. 16, 2022

Related U.S. Application Data

(60) Provisional application No. 63/191,017, filed on May 20, 2021, provisional application No. 63/124,400, filed on Dec. 11, 2020.

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0482* (2013.01); *A61B 17/062* (2013.01);
(Continued)

(58) Field of Classification Search
CPC ............ A61B 17/0469; A61B 17/0482; A61B 17/062; A61B 17/0057; A61B 17/0491;
(Continued)

(56) References Cited

U.S. PATENT DOCUMENTS

| 6,641,592 B1 | 11/2003 | Sauer et al. |
| 7,341,595 B2 | 3/2008 | Hinchliffe et al. |

(Continued)

OTHER PUBLICATIONS

Terumo Medical Corporation, Angio-Seal® Vascular Closure Device Online Brochure, Copyright 2022, Terumo Medical Corporation, Somerset, New Jersey, 5 pages.
(Continued)

*Primary Examiner* — Sarah A Long
*Assistant Examiner* — James R McGinnity
(74) *Attorney, Agent, or Firm* — Rooney IP, LLC

(57) ABSTRACT

A vessel closure device including a proximal end including a handle with first and second actuators, a distal end including a suturing mechanism, and first and second needles associated with the suturing mechanism. At least one of the first and second needles is coupled to the first actuator. The second actuator is coupled to the suturing mechanism. The suturing mechanism includes a pivotal element capable of being moved by the second actuator between an insertion and removal orientation, a first deployed orientation, and a second deployed orientation. The suturing mechanism is activated within the vessel through an opening in the wall of the vessel and the first and second needles are directed through the vessel wall adjacent to the opening to direct a tensile member adjacent to the opening for closing and sealing the opening.

33 Claims, 21 Drawing Sheets

(51) Int. Cl.
    *A61B 17/00* (2006.01)
    *A61B 17/06* (2006.01)
(52) U.S. Cl.
    CPC . *A61B 2017/00367* (2013.01); *A61B 17/0057* (2013.01); *A61B 17/0491* (2013.01); *A61B 2017/0496* (2013.01); *A61B 17/06066* (2013.01)
(58) Field of Classification Search
    CPC .... A61B 17/06066; A61B 2017/00367; A61B 2017/0496; A61B 2017/0472; A61B 17/0625
    See application file for complete search history.

(56) References Cited

U.S. PATENT DOCUMENTS

| | | | |
|---|---|---|---|
| 9,895,146 B1 | 2/2018 | Al-Jazaeri | |
| 2002/0016602 A1 | 2/2002 | Li et al. | |
| 2006/0069397 A1* | 3/2006 | Nobles | A61B 17/0057 606/144 |
| 2008/0269786 A1* | 10/2008 | Nobles | A61B 17/0057 606/144 |
| 2010/0030242 A1* | 2/2010 | Nobles | A61B 17/0469 606/147 |
| 2010/0145364 A1 | 6/2010 | Keren et al. | |
| 2012/0071901 A1 | 3/2012 | Heneveld | |
| 2013/0178872 A1* | 7/2013 | Shriver | A61B 17/0625 606/148 |
| 2013/0310853 A1* | 11/2013 | Zaugg | A61B 17/0401 606/232 |
| 2014/0249552 A1 | 9/2014 | Tang et al. | |
| 2017/0071599 A1* | 3/2017 | Malkowski | A61B 17/0482 |
| 2018/0228478 A1* | 8/2018 | Fortson | A61B 17/0057 |
| 2019/0008506 A1* | 1/2019 | Kurd | A61B 17/06004 |
| 2020/0093478 A1* | 3/2020 | Caffes | A61B 17/0485 |

OTHER PUBLICATIONS

Abbott, Perclose ™ Prostyle™ Suture-Mediated Closure and Repair System Online Brochure, Copyright 2022, Abbott, Abbott Park, Illinois, 24 pages.
Teleflex, Mantar® Vascular Closure Device Online Brochure, Copyright 2020, Wayne, Pennsylvania, 8 pages.
Veryan Medical, Celt ACD® Vascular Closure Device Online Product Description, Copyright 2022, Veryan Medical, Horsham, West Sussex, United Kingdom, 3 pages.
Syed M Hussain Md, Prospective Evaluation of The CELT Arterial Closure Device in an Outpatient Based Catheterization Laboratory Presentation, Apr. 18, 2019, Champaign, Illinois, 14 pages.
Cordis, Mynx Control® Vascular Closure Device Step-by-Step Guide Online Brochure, Copyright 2021, Cordis, Santa Clara, California, 2 pages.
U.S. Patent and Trademark Office, International Search Report and Written Opinion in PCT Serial No. PCT/US2021/062671, Mar. 2, 2022; 10 pages.
U.S. Patent and Trademark Office, International Search Report and Written Opinion in PCT Serial No. PCT/US2021/062667, Mar. 2, 2022; 10 pages.
U.S. Patent and Trademark Office, International Preliminary Report on Patentability in related PCT/US2021/062671, Jul. 13, 2023.
U.S. Patent and Trademark Office, International Preliminary Report on Patentability in related PCT/US2021/062667, Jul. 25, 2023.

* cited by examiner

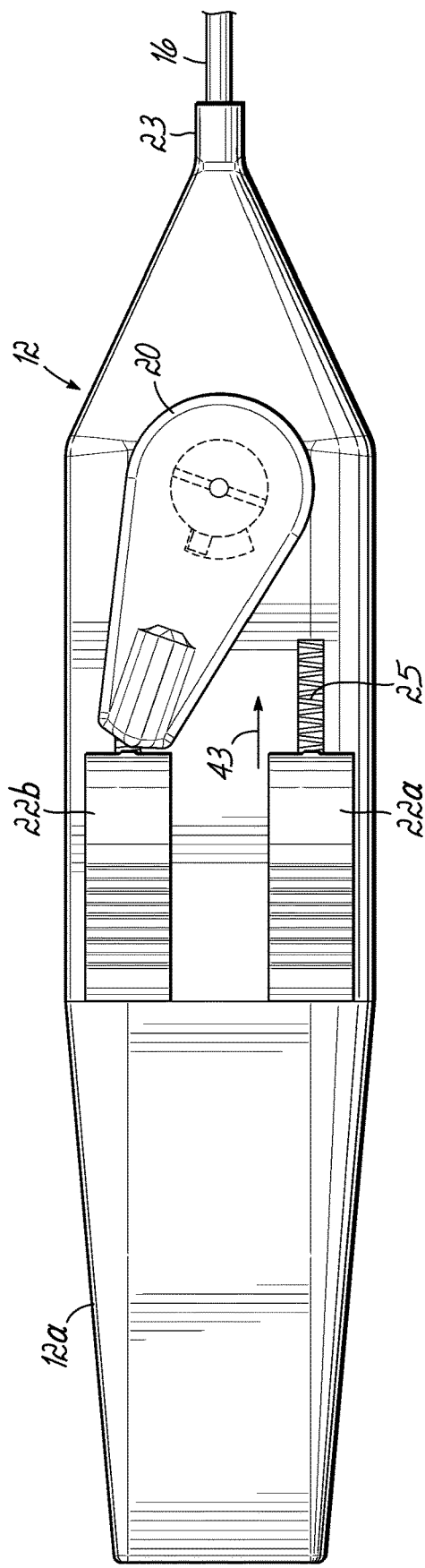
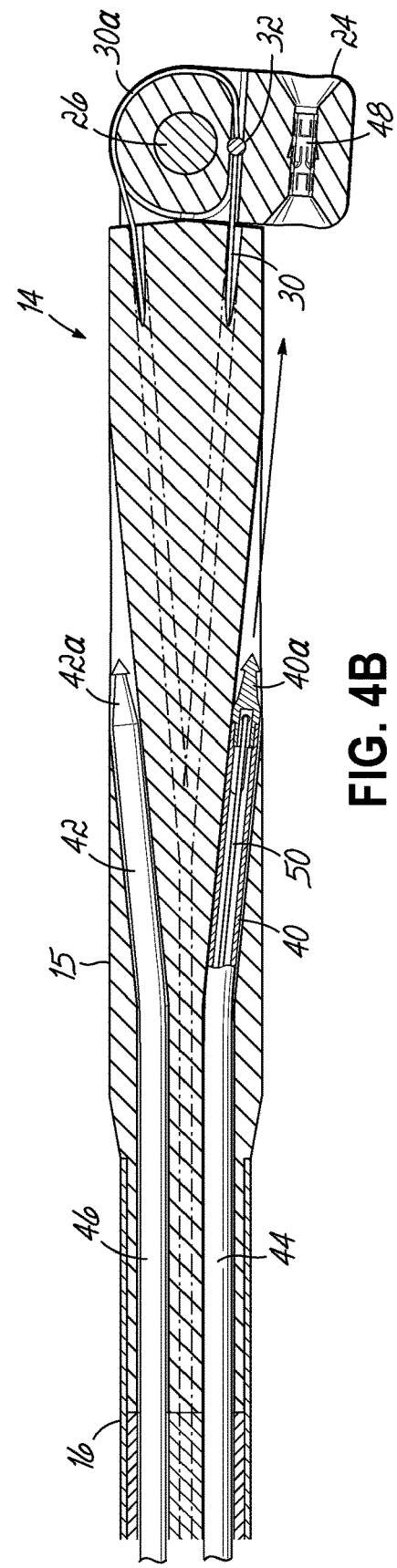
FIG. 4A
FIG. 4B

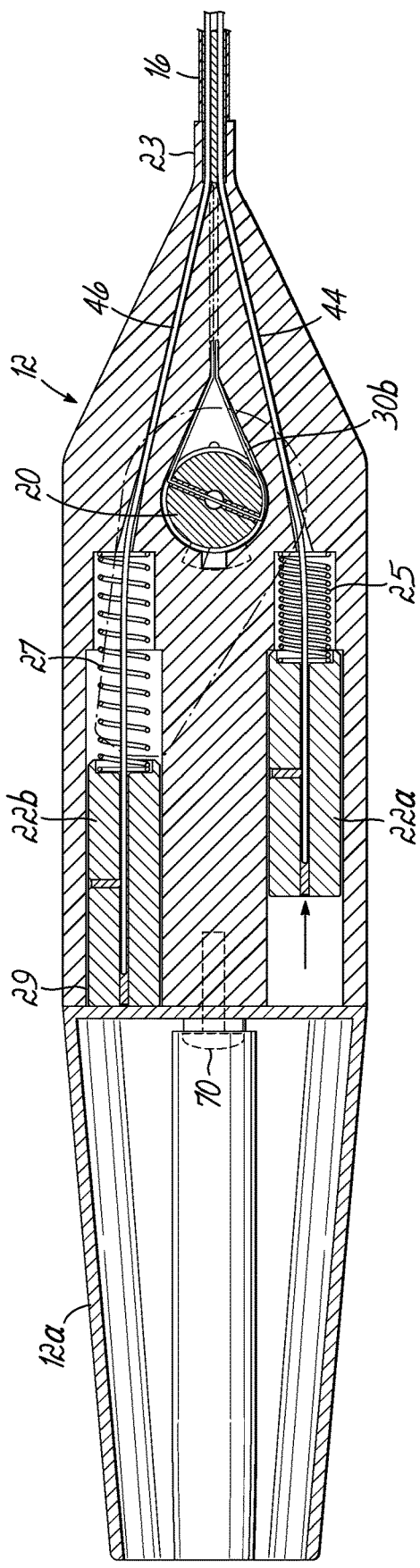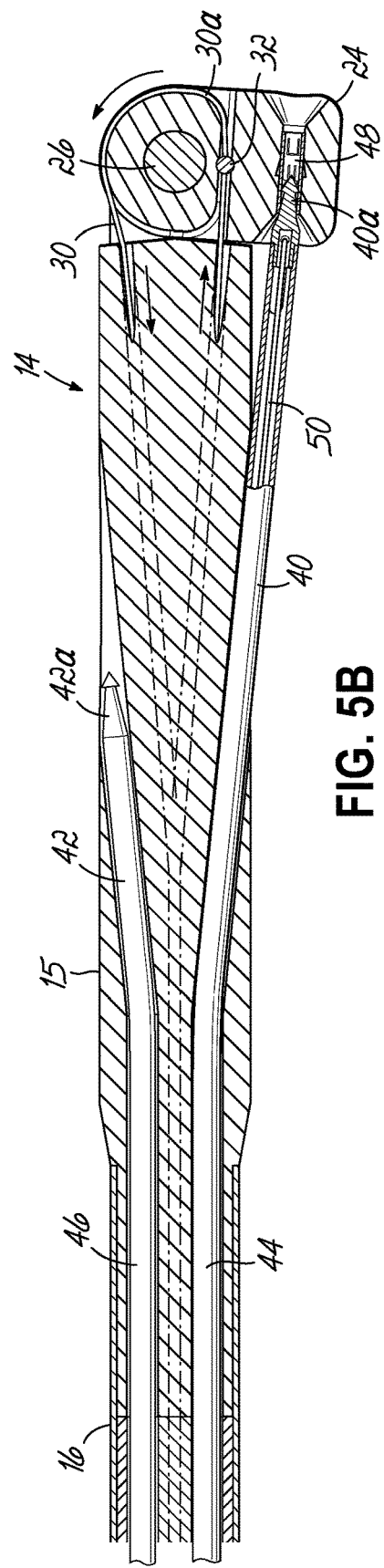
FIG. 5A
FIG. 5B

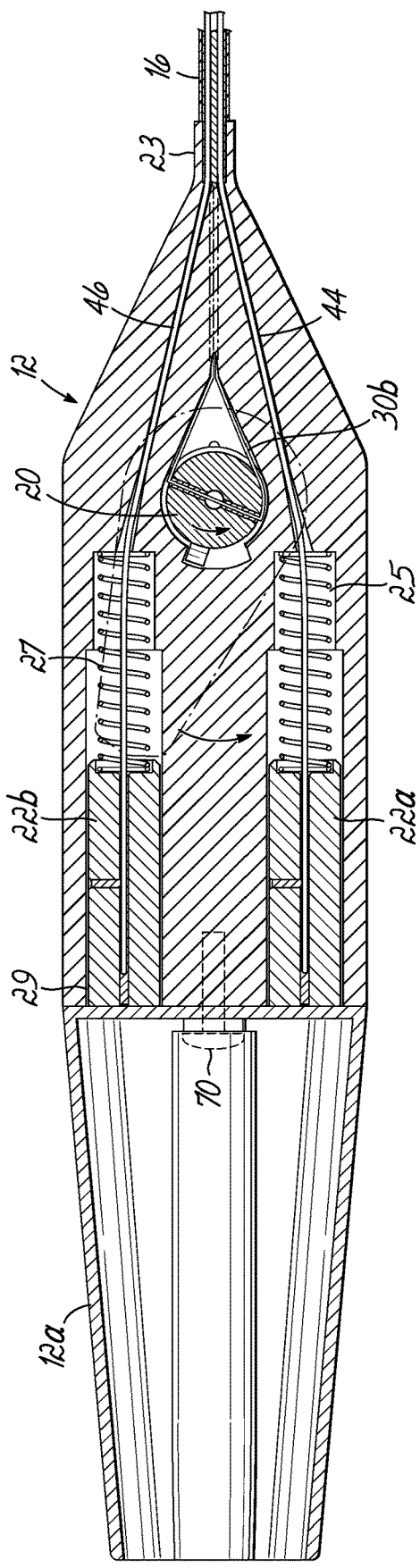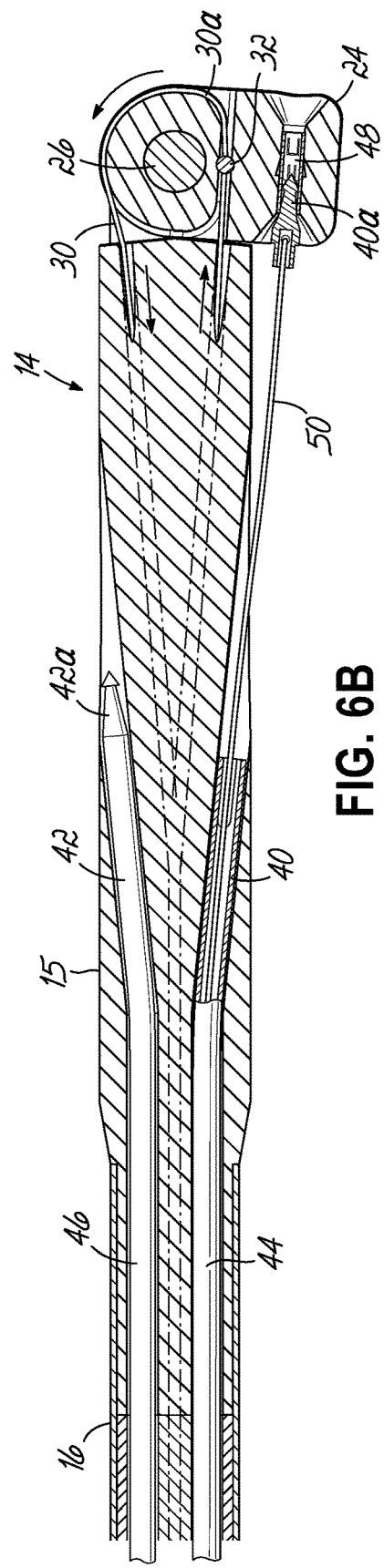
FIG. 6A
FIG. 6B

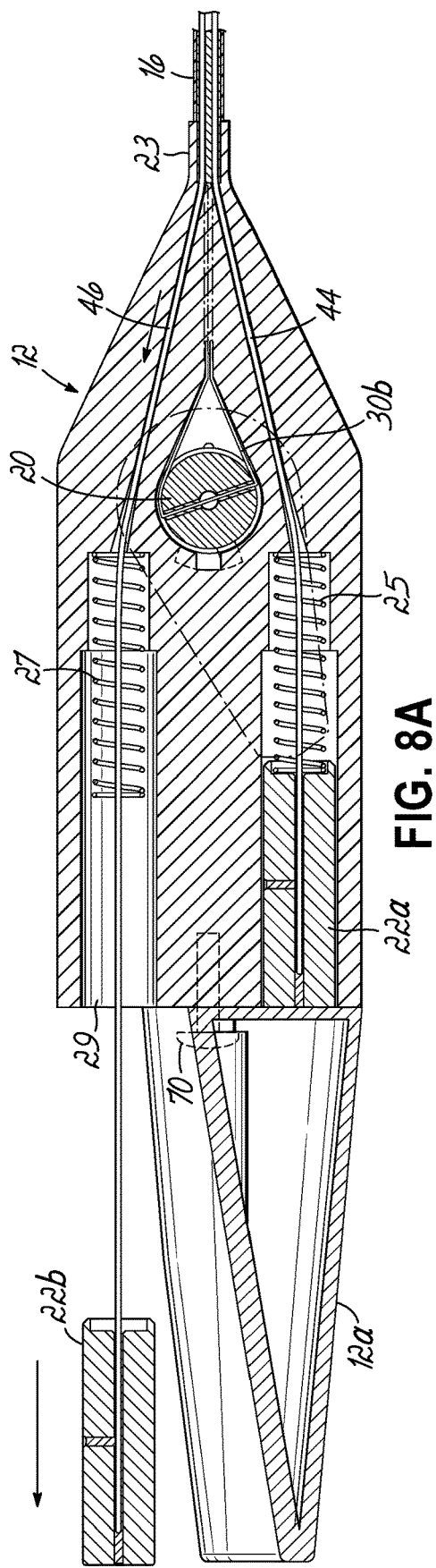
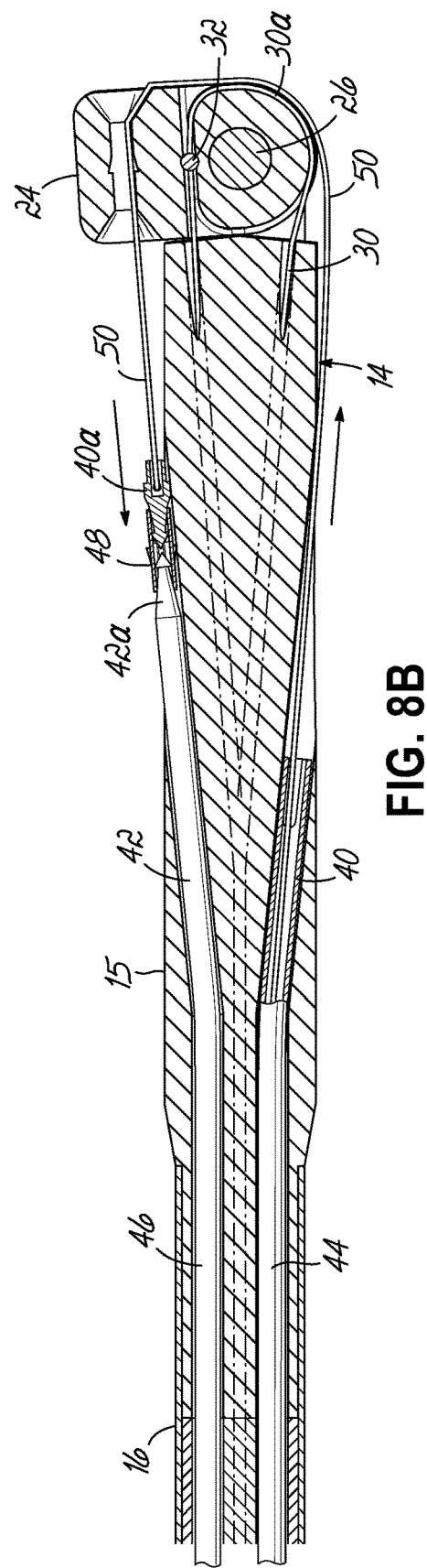
FIG. 8A
FIG. 8B

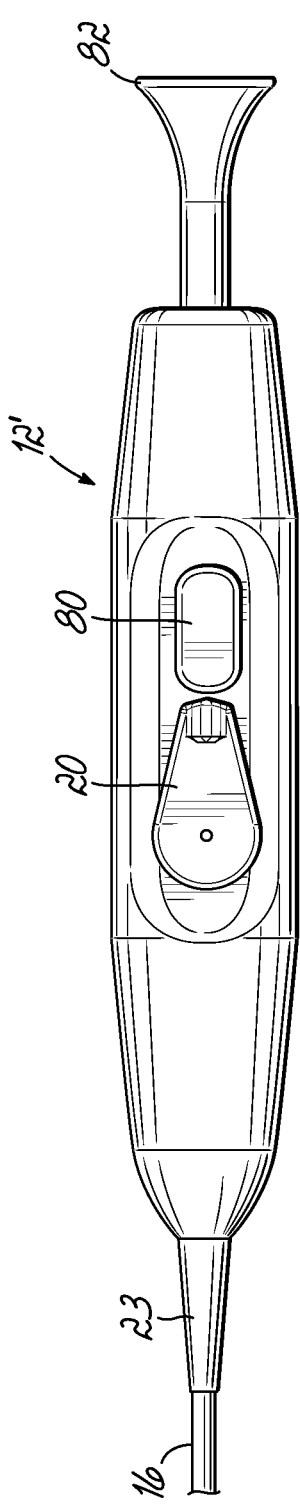
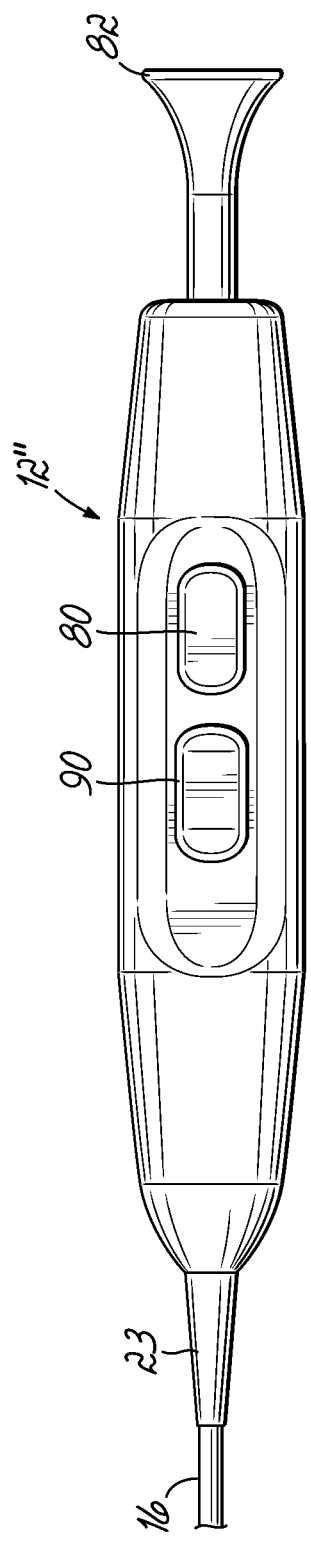
FIG. 12
FIG. 13

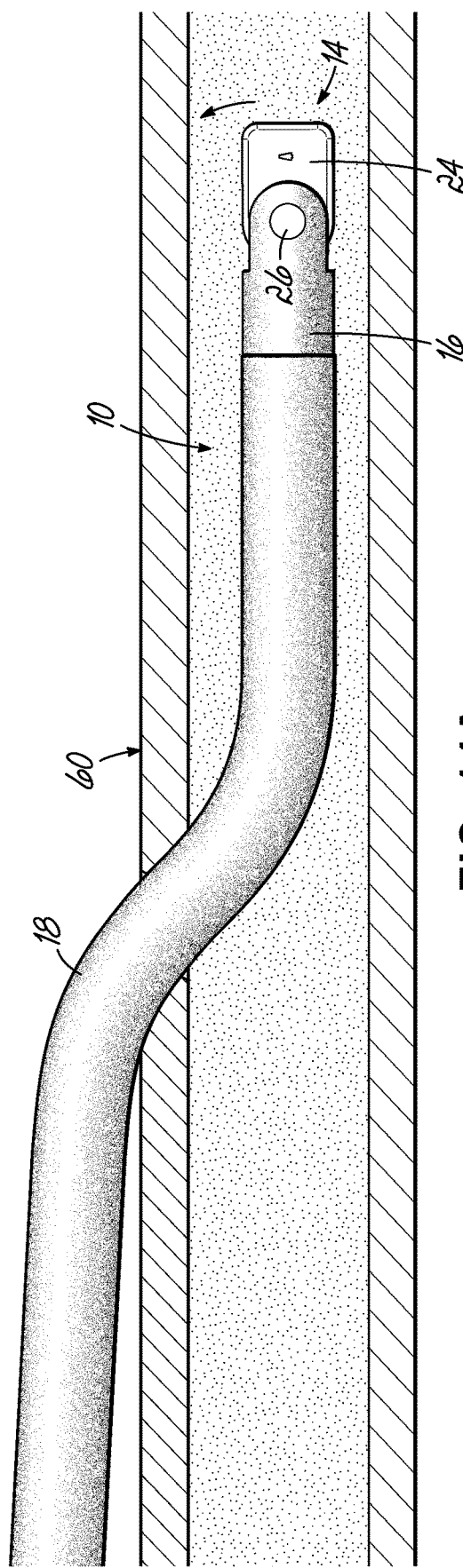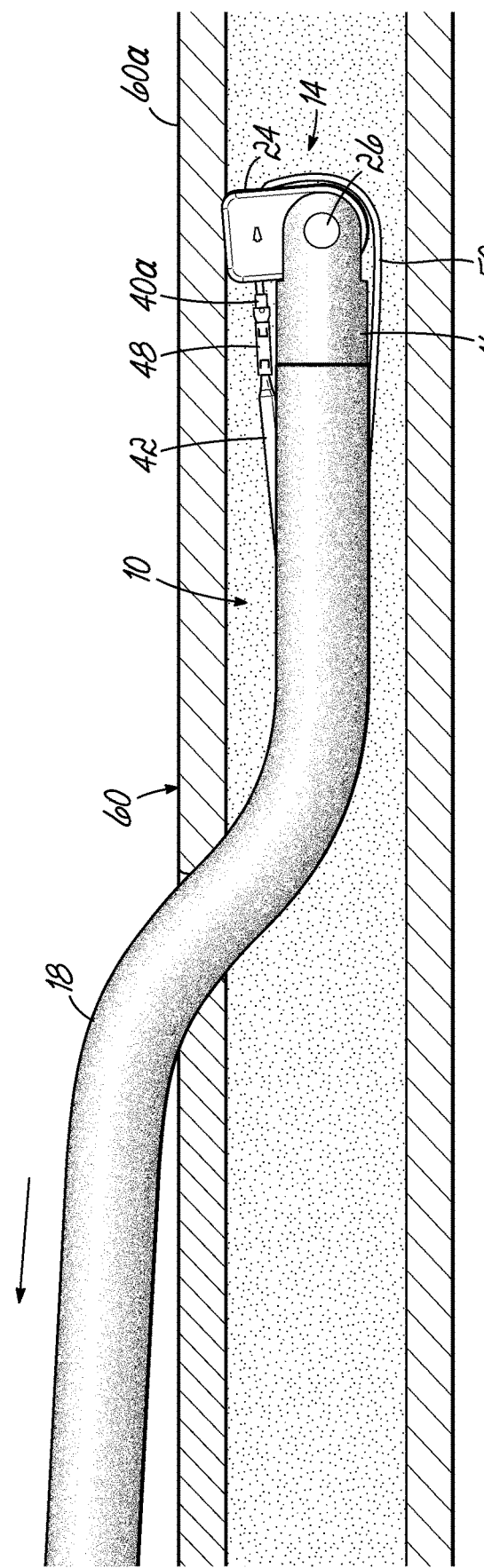

VESSEL CLOSURE DEVICES AND METHODS

CROSS REFERENCE TO RELATED APPLICATIONS

This application claims priority to U.S. Provisional Patent Application Ser. No. 63/124,400, filed on Dec. 11, 2020 and U.S. Provisional Patent Application Ser. No. 63/191,017, filed May 20, 2021, the disclosures of which are hereby incorporated herein by reference in their entirety.

TECHNICAL FIELD

The present invention generally relates to closure devices and methods for sealing punctures or other openings in blood vessels, such as the common carotid artery, made during a direct access approach for neurological therapy. The devices and methods may be used in the course of other therapies or surgical procedures as well.

BACKGROUND

Vascular access for neuro-therapy is traditionally performed through the femoral artery or radial access approaches. For vascular access to the brain using a traditional approach, neuro-therapy devices must navigate through lengthy tortuous segments of the anatomy to gain access to the therapeutic site. The Direct Carotid Artery Puncture (DCP) method for accessing the common carotid artery allows doctors quicker access to the brain and eliminates the need for devices that must traverse the typical femoral interventional track. Given these benefits, it would be further advantageous to seal the puncture from this DCP method in a more efficient and effective manner.

To close and seal a DCP, doctors currently may apply a suture manually prior to the access or may simply apply direct pressure to the site after intervention until the vessel seals itself. The latter method relies on blood coagulation at the puncture site. Therefore, the time period necessary for closing the puncture with direct pressure may be quite lengthy. Also, this method may be less than effective because of the lack of suitable anatomy in the vicinity of the common carotid artery against which the pressure may be applied. Moreover, the common carotid artery carries blood at a high pressure (100 to 200 mmHg) which further complicates the ability to effectively close the carotid puncture with current methods.

SUMMARY

Generally, a vessel closure device is provided and includes a proximal end including a handle with first and second actuators, a distal end including a suturing mechanism, and first and second needles associated with the suturing mechanism. At least one of the first and second needles is coupled to the first actuator. The second actuator is coupled to the suturing mechanism and the suturing mechanism includes a pivotal element capable of being moved by the second actuator between an insertion and removal orientation, a first deployed orientation, and a second deployed orientation. The suturing mechanism is activated within the vessel through an opening in the wall of the vessel and the first and second needles are directed through the vessel wall adjacent to the opening to direct a tensile member adjacent to the opening for closing and sealing the opening.

In some embodiments, the first actuator of the vessel closure device may be spring-biased into a position for retracting at least one of the first and second needles. The vessel closure device may include a third actuator where the first needle is coupled to the first actuator, and the second needle is coupled to the third actuator. The third actuator may be spring-biased into a position for retracting the second needle.

In an alternate embodiment, the vessel closure device includes a proximal end including a handle with first, second, and third actuators, a distal end including a suturing mechanism, a first needle associated with the suturing mechanism and coupled to the first actuator, and a second needle associated with the suturing mechanism and coupled to the second actuator. The third actuator is coupled to the suturing mechanism and the suturing mechanism includes a pivotal element capable of being moved by the third actuator between an insertion and removal orientation, a first deployed orientation, and a second deployed orientation. The suturing mechanism is deployed within the vessel through an opening in the wall of the vessel while the pivotal element is in the insertion and removal orientation. The first needle is directed through the vessel wall adjacent to the opening to direct a tensile member adjacent to the opening using the first actuator while the pivotal element is in the first deployed orientation. The second needle is directed through the vessel wall adjacent to the opening to direct a tensile member adjacent to the opening using the second actuator while the pivotal element is in the second deployed orientation, and the tensile member is used for closing and sealing the opening.

In some embodiments, the first actuator of the vessel closure device may be spring-biased into a position for retracting the first needle. The second actuator may be spring-biased into a position for retracting the second needle.

In alternate or additional aspects, the suturing mechanism may include a coupling member having first and second ends, the first end being capable of coupling to the first needle and the second end being capable of coupling to the second needle. The first needle may include a detachable tip coupled to the tensile member. The vessel closure device may include an elongate shaft coupled between the handle and the suturing mechanism. The vessel closure device may include a flexible strain relief coupled between the handle and the elongate shaft.

In alternate or additional aspects, at least one of the first and second deployed orientations of the vessel closure device may be an angled orientation. In some embodiments, the pivotal element may extend in generally opposite directions in the first and the second deployed orientations. The vessel closure device may include an introducer sheath through which the suturing mechanism may be directed into a blood vessel and the sheath can then be withdrawn from the blood vessel with the suturing mechanism remaining in the blood vessel thereby inhibiting blood from exiting the blood vessel through the opening.

A method of closing an opening in a vessel is provided and includes directing a suturing mechanism, which includes a pivotal element, through the opening and into the vessel interior while the pivotal element is in an insertion and removal orientation, deploying the pivotal element of the suturing mechanism into a first deployed orientation after the suturing mechanism is positioned within the interior of the vessel and directing a first needle through the vessel wall adjacent to the opening using the suturing mechanism. The pivotal element of the suturing mechanism is deployed into a second deployed orientation and a second needle is directed through the vessel wall adjacent to the opening using the suturing mechanism. A tensile member is directed through the vessel wall adjacent to the opening using the suturing mechanism. The pivotal element is returned to the insertion and removal orientation and the suturing mechanism is withdrawn from the vessel. The tensile member is used to close the opening in the vessel.

In some embodiments, the vessel may be a blood vessel, and the method may include directing an introducer sheath into an opening of a blood vessel, directing the suturing mechanism through the introducer sheath and into the interior of the blood vessel, and withdrawing the introducer sheath from the blood vessel with the suturing mechanism remaining in the blood vessel thereby inhibiting blood from exiting the blood vessel through the opening. The suturing mechanism may include a coupling member having first and second ends, and the method may include coupling the first needle to the first end, coupling the second needle to the second end, retracting the first and second needles, and pulling the tensile member through the vessel wall.

BRIEF DESCRIPTION OF DRAWINGS

FIG. 4A is a perspective view of the handle at the proximal end of the suturing device of FIGS. 1 and 2.

FIG. 4B is a cross-section view of the suturing mechanism of FIGS. 2A, 2B, and 2C.

FIG. 5A is a cross-section view of the handle at the proximal end of the suturing device of FIGS. 1 and 2.

FIG. 5B is a cross-section view of the suturing mechanism of FIGS. 2A, 2B, and 2C.

FIG. 6A is a cross-section view of the handle at the proximal end of the suturing device of FIGS. 1 and 2.

FIG. 6B is a cross-section view of the suturing mechanism of FIGS. 2A, 2B, and 2C.

FIG. 8A is a cross-section view of the handle at the proximal end of the suturing device of FIGS. 1 and 2.

FIG. 8B is a cross-section view of the suturing mechanism of FIGS. 2A, 2B, and 2C.

FIG. 12 is a first alternative embodiment of a handle.

FIG. 13 is a second alternative embodiment of a handle.

FIGS. 14A and 14B illustrate the suturing device exchanged internally with the introducer sheath while within a blood vessel.

DETAILED DESCRIPTION

The device disclosed herein generally allows a single-suture closure of a blood vessel, such as the common carotid artery or another vessel, via a minimally invasive percutaneous approach. There are various non-limiting aspects that may be used alone or in any desired combination. The suturing device may be tracked through an introducer sheath thereby allowing an internal exchange of the suturing device and the introducer sheath. This will inhibit (that is, eliminate, or at least substantially reduce), blood loss normally experienced during a typical device exchange as a result of the high blood pressures found in the common carotid artery. These pressures may be 100 mmHg to 200 mmHg or more. In comparison, typical arterial pressures in a femoral or radial exchange are in the range of 80 mmHg to 160 mmHg. The suturing device may generally include a proximally located handle, suture needles, sutures or other tensile members, suture transfer mechanisms and, optionally, a blood flow visual indicator. As used herein to describe various embodiments from the perspective of a user of a suturing device, "proximal" may refer to a direction generally towards the user of the device, while "distal" may refer to a direction generally away from the user of the device. The sutures may be percutaneously routed through the dermis skin layer and the vessel wall without affecting the epidermis or outer skin layer.

Figure 1:
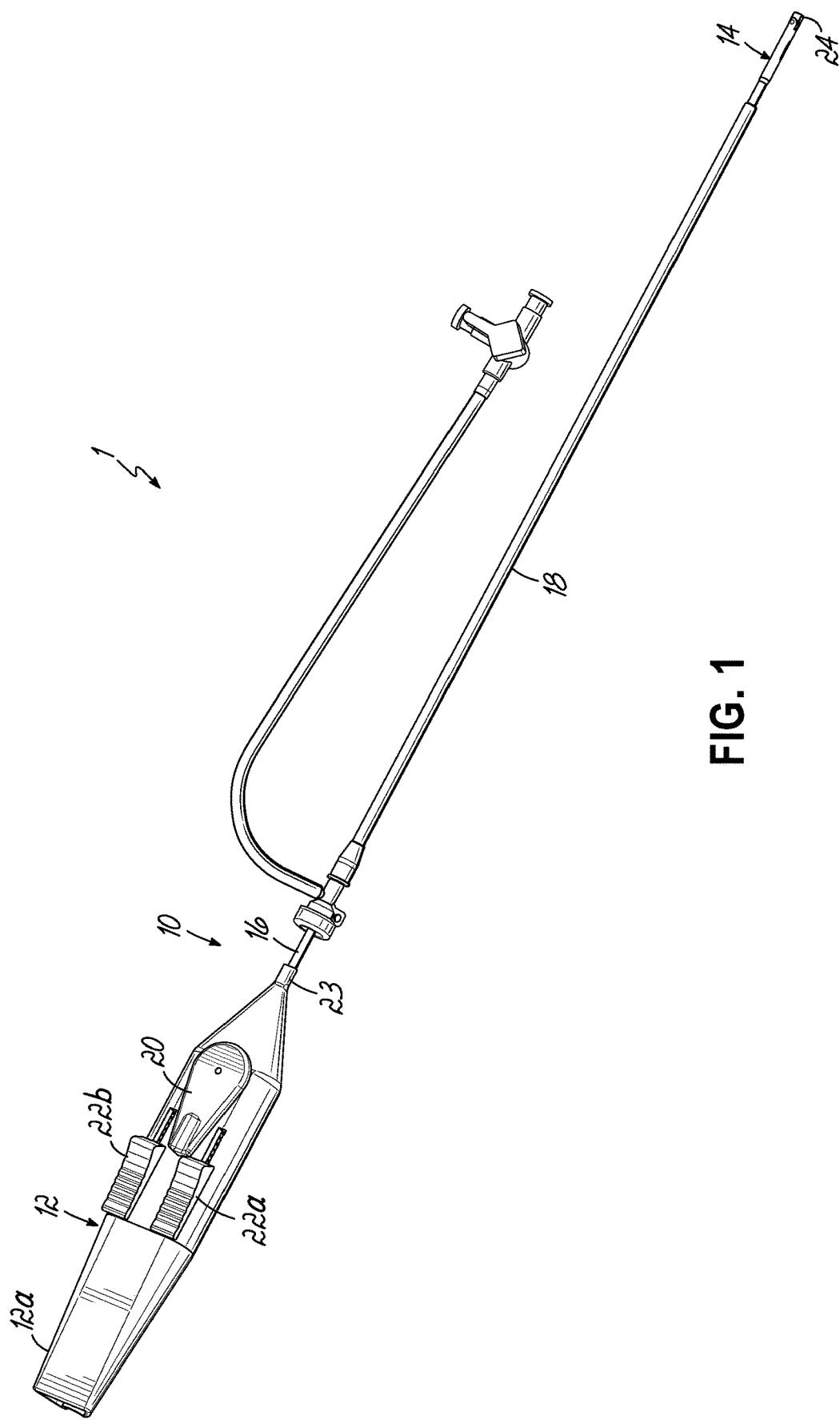
FIG. 1 is a perspective view of an exemplary suturing device with an introducer sheath.
Figure 2:
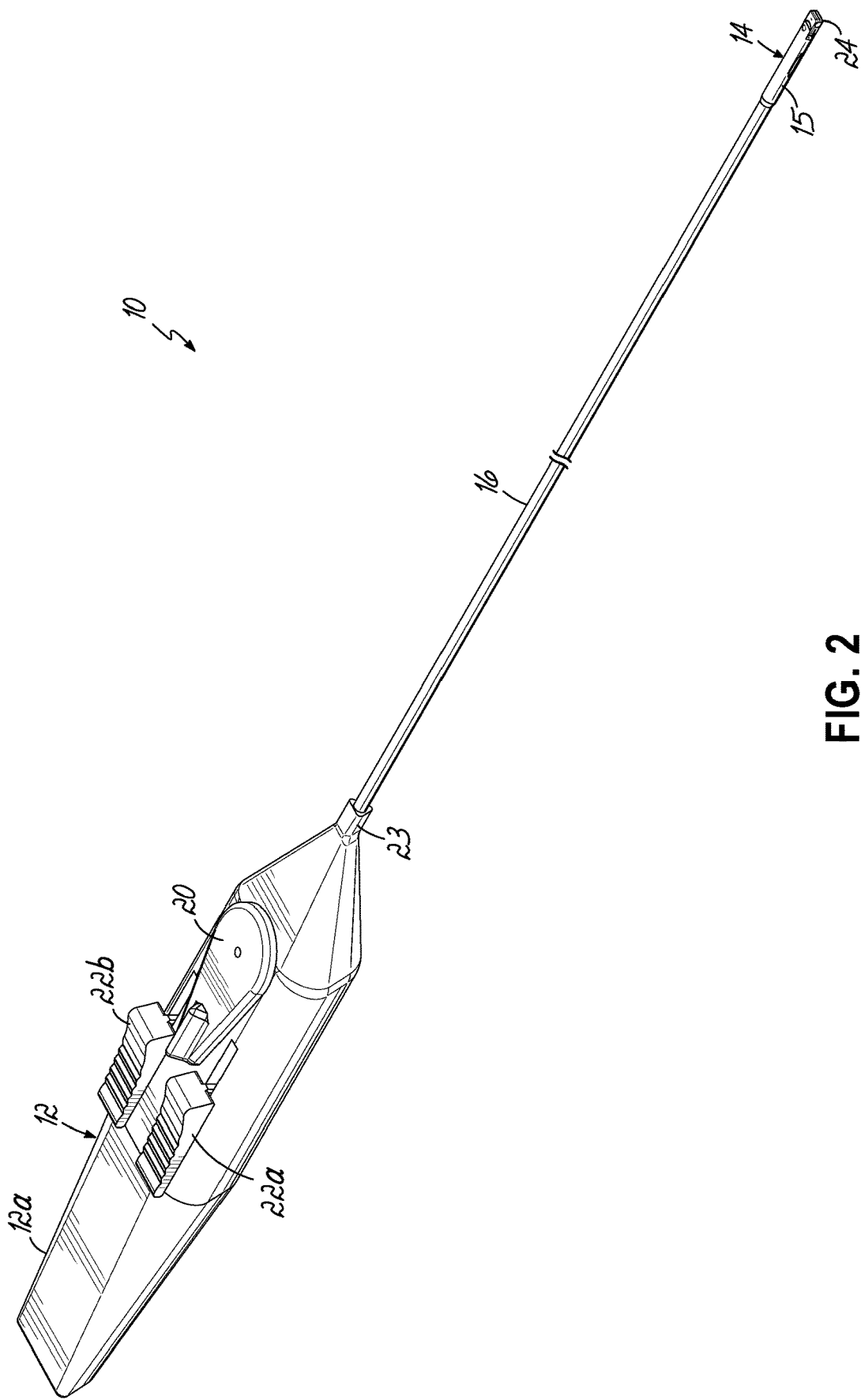
FIG. 2 is an alternate perspective view of the exemplary suturing device of FIG. 1 without the introducer sheath.

FIGS. 1 and 2 illustrate a first exemplary embodiment of a system 1 that includes a suturing device 10. The suturing device 10 generally includes a handle 12 at a proximal end and a suturing mechanism 14 at the distal end. As used herein, "suture", "suturing" and similar forms of these terms mean any flexible tensile element or member regardless of form or material and suitable for approximating tissue. As used herein, "tensile member" may be a mono-filament suture, a multi-filament suture, a metallic suture, or any other suitable tensile member. An elongate, narrow shaft 16 extends between the handle 12 and the suturing mechanism 14. The system 1 further includes an introducer sheath 18 through which the shaft 16 is directed during a suturing procedure as further described below. The handle 12 includes one or more actuating mechanisms necessary for operating the suturing mechanism 14 and the suturing needles (described below). For example, these include a pivoting, lever type actuator 20 operating the suturing mechanism 14 and respective actuators 22a, 22b that move the suturing needles (shown and described herein below). While these actuators 20, 22a, 22b are shown and described as manually driven, one or more of the actuators may be motorized, mechanically leveraged or assisted in other manners. A flexible strain relief 23 is fixed generally between the relatively rigid handle 12 and the more flexible shaft 16 to more evenly distribute forces between these components.

Figure 2A:
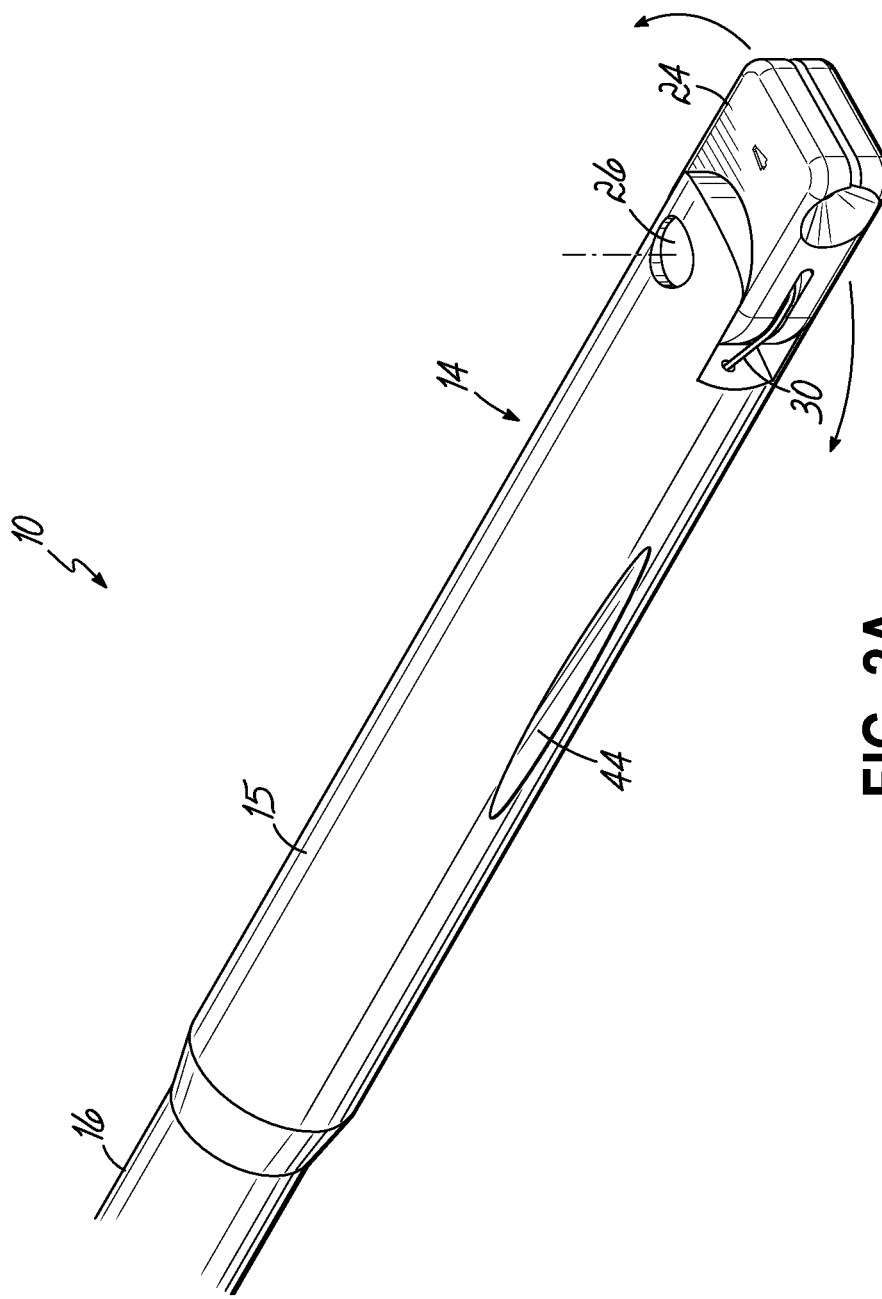
FIGS. 2A, 2B, and 2C are perspective views of the distal end of the exemplary suturing device of FIGS. 1 and 2, and specifically, a shaft, needle guide, and suturing mechanism.
Figure 2C:
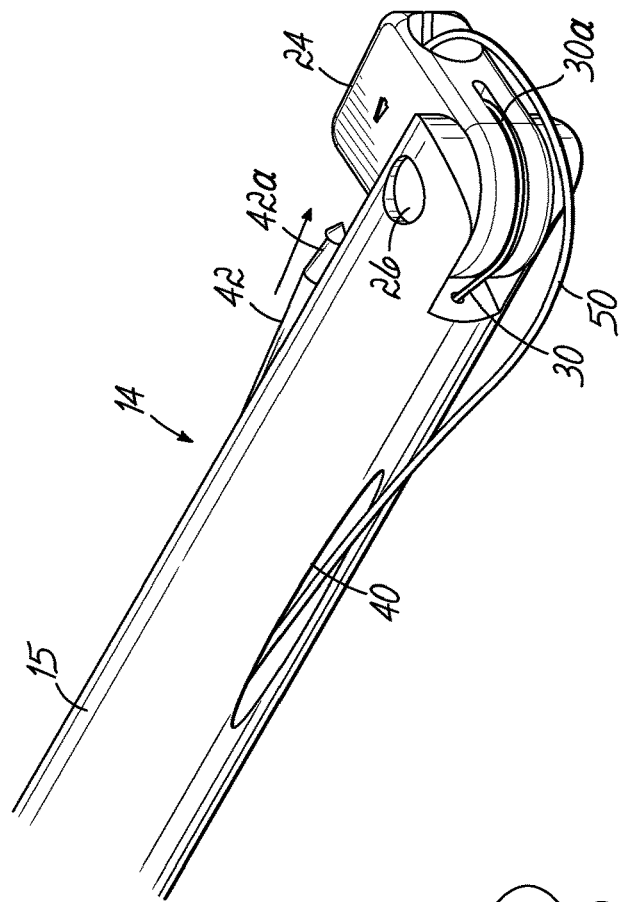
Figure 2B:
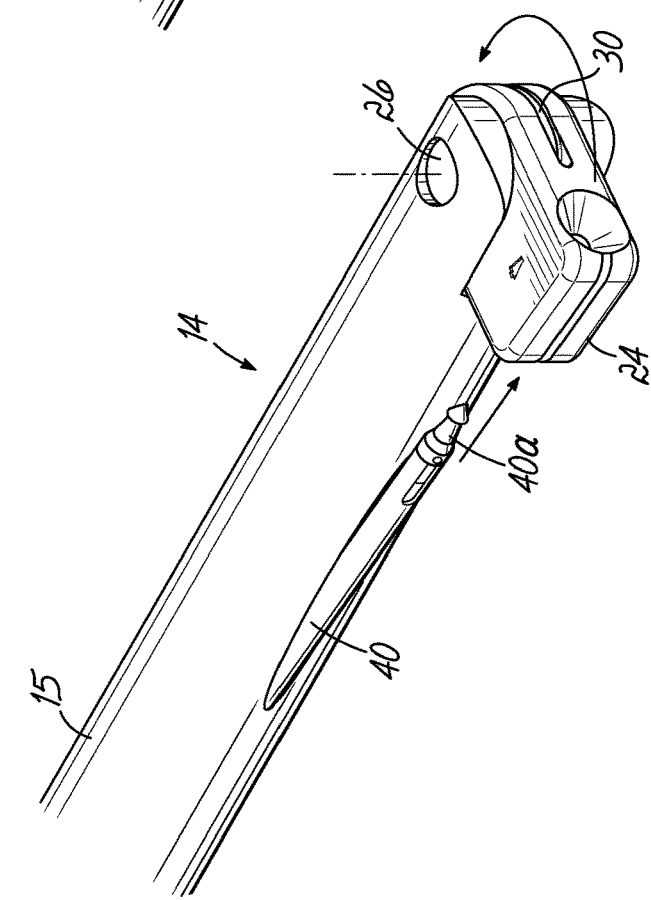

FIGS. 2A, 2B and 2C are perspective views of the distal end of the shaft 16 and, specifically, the suturing mechanism 14. The suturing mechanism 14 includes a needle guide 15 and a pivotal element 24. This pivotal element 24 is secured to the distal end of the needle guide 15 by a pivot 26 that allows the pivotal element 24 to pivot between an orientation, shown in FIG. 2A, that essentially aligns the lengthwise extent of the pivotal element 24 with the needle guide 15 and respective transverse orientations with respect to the lengthwise axis of the needle guide 15 as shown in FIGS. 2B and 2C. As will become apparent from the description below, the transverse orientations of the pivotal element 24 facilitate a suturing procedure performed from within a blood vessel. As used herein, the term "vessel", "blood vessel", "arteries", "veins", and similar forms of these terms mean any component of the circulatory system that transports blood throughout the human body. The aligned orientation of the pivotal element 24 shown in FIG. 2A is an insertion and removal orientation as will be understood from the description to follow. The transverse orientations of the pivotal element 24 shown in FIGS. 2B and 2C are facilitated by pivoting the lever 20 as will be described below.

Figure 3A:
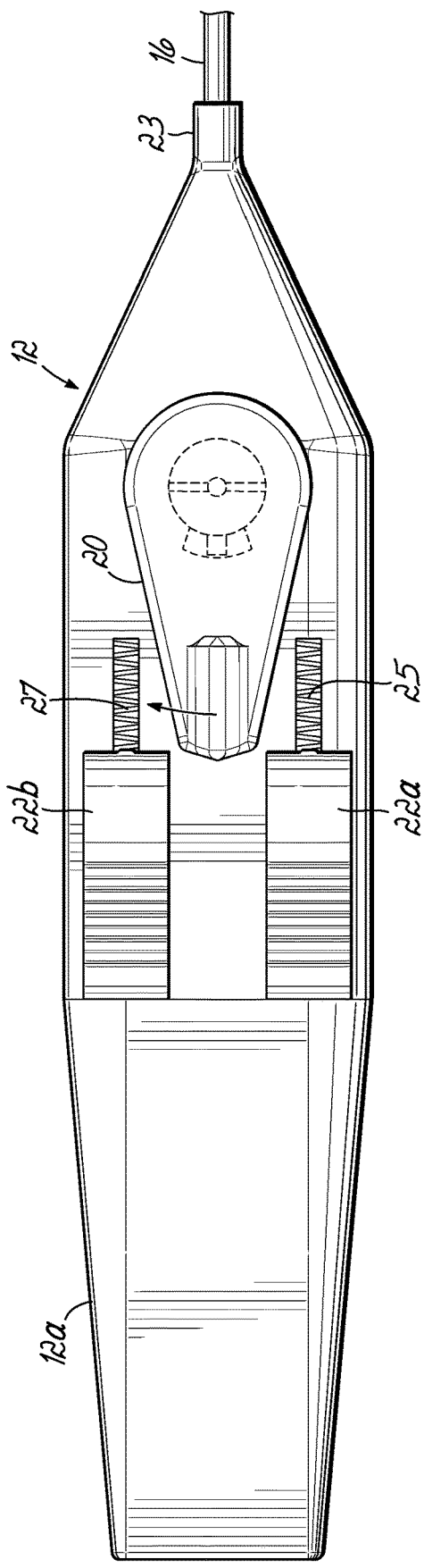
FIG. 3A is a perspective view of the handle at the proximal end of the suturing device of FIGS. 1 and 2.
Figure 3B:
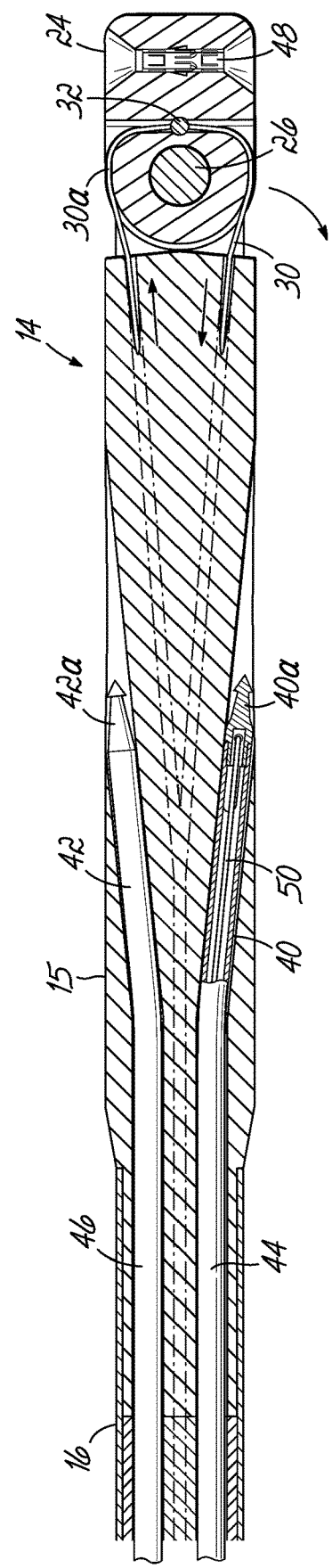
FIG. 3B is a cross-section view of the suturing mechanism of FIGS. 2A, 2B, and 2C.
Figure 7A:
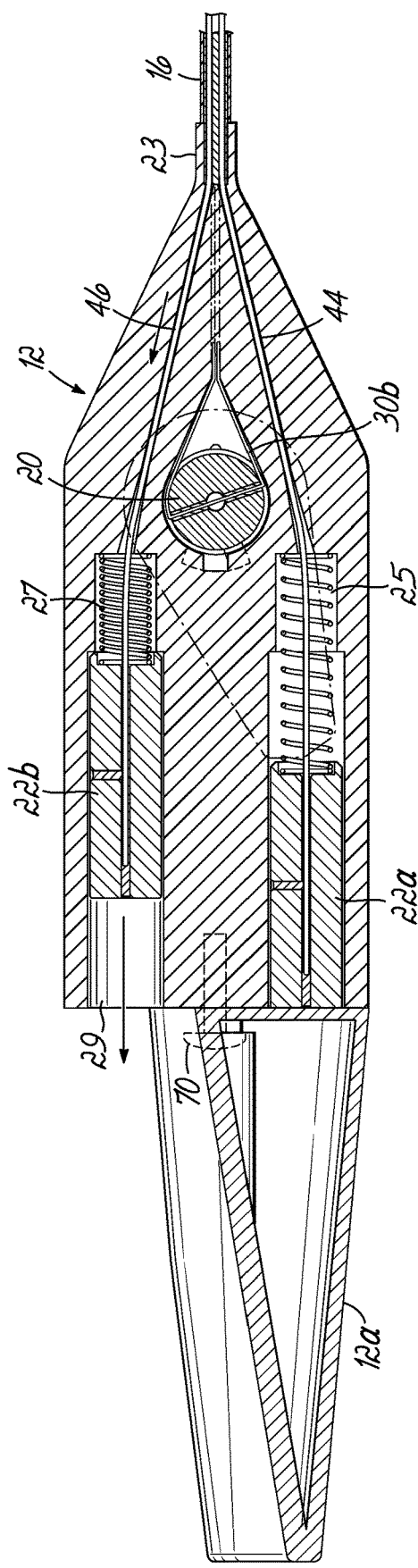
FIG. 7A is a cross-section view of the handle at the proximal end of the suturing device of FIGS. 1 and 2.
Figure 7B:
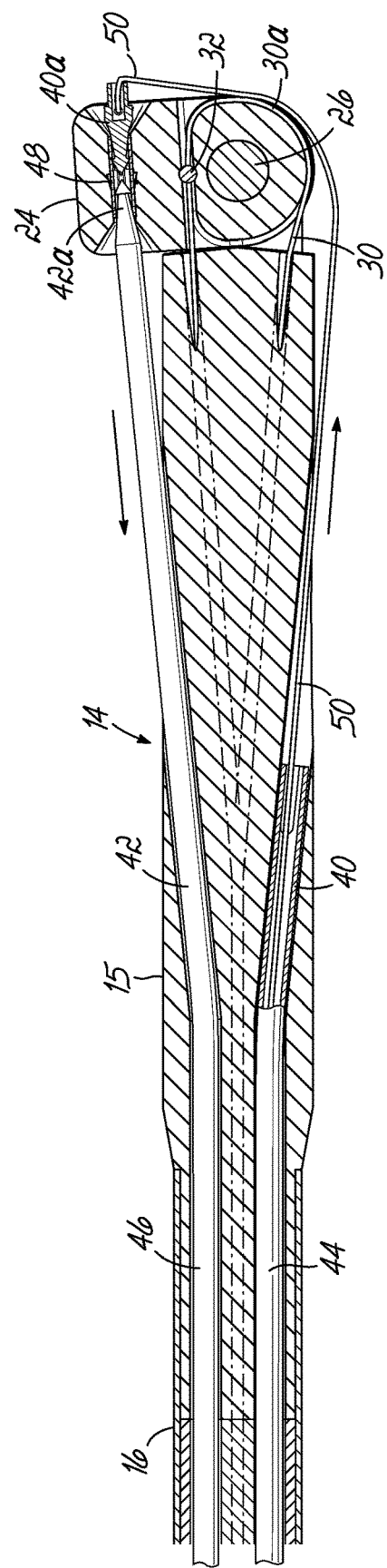
FIG. 7B is a cross-section view of the suturing mechanism of FIGS. 2A, 2B, and 2C.
Figure 9:
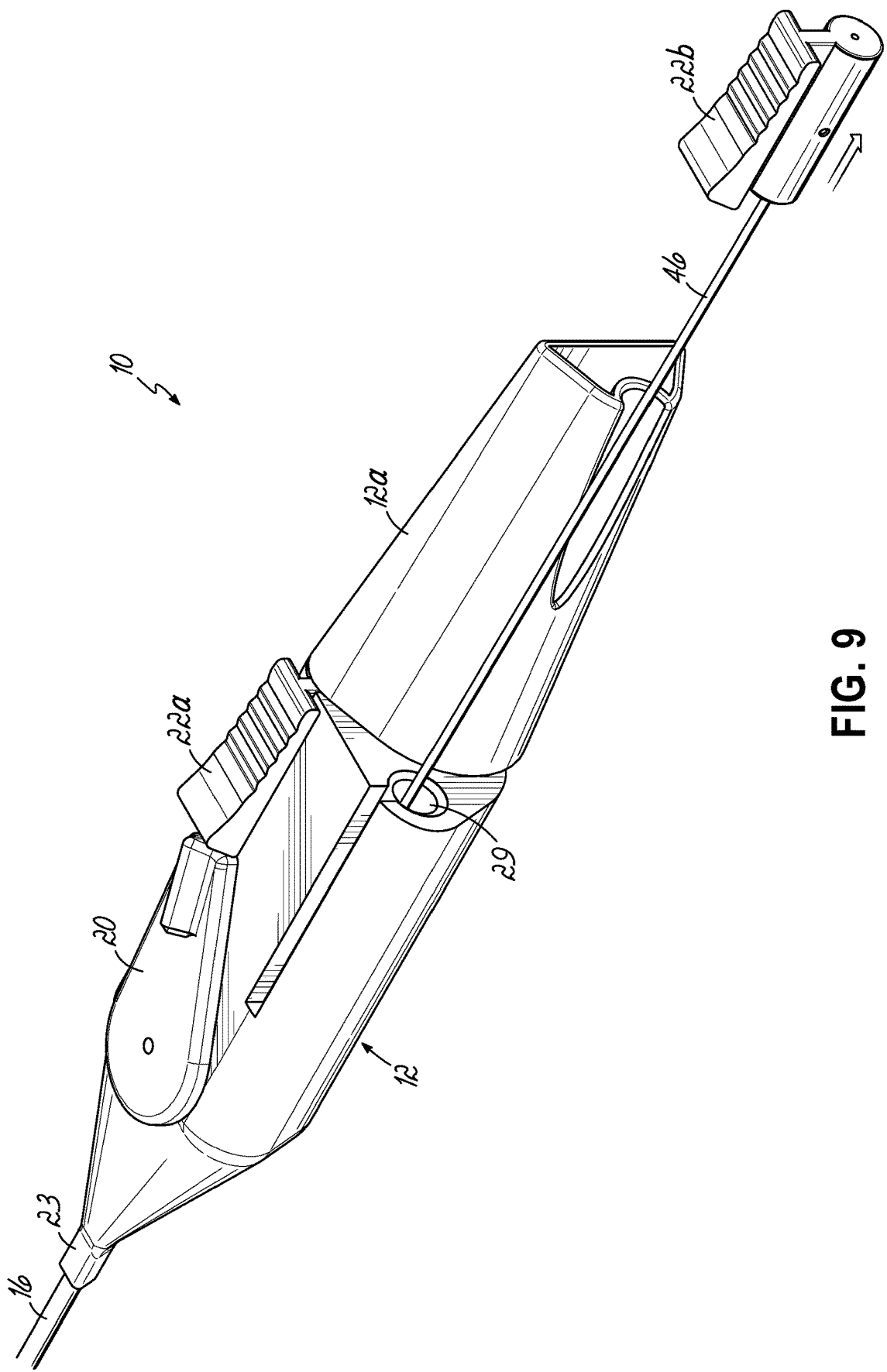
FIG. 9 is a perspective view of the proximal end of the handle of the suturing device of FIGS. 1 and 2.

FIGS. 3A and 3B are respective views of the handle 12 at the proximal end of the device 10 and the suturing mechanism 14 at the distal end of the device 10. FIGS. 4A, 4B, 5A, 5B, 6A, 6B, 7A, 7B, 8A, 8B and 9 progressively illustrate additional structure and function or methodology of the device 10. The lever 20 is pivoted or rotated in a first direction (see arrow in FIG. 3A) to pivot or rotate the pivotal element 24 at the distal end (see arrow, FIG. 3B). The lever 20 is coupled to the pivotal element 24 by an actuating wire 30. As shown in FIGS. 3B, 5B, and 7B, a loop 30a of the wire 30 is fixed at a point 32 to the pivotal element 24 and, as shown best in FIGS. 5A and 7A, another loop 30b is fixed for rotation with the lever 20. The pivotal element 24 includes a flexible coupling member 48.

Referring to FIGS. 3A and 3B, the distal end of the device 10 includes two needles 40, 42 which are either fully integral with or fixedly coupled to respective wires 44, 46. Needle 40 is a two-piece needle which has a needle tip 40a detachable from a needle body 40b by way of a friction fit, for example. Needle 42 has an integral (i.e., fixed) tip 42a. The word "integral" here encompasses fully integral constructions as well as constructions in which the tip 42a is fixedly (i.e., not "removably") coupled to the remainder of the integral needle 42. The two needles 40, 42 are either fully integral with or fixedly coupled to respective wires 44, 46, except for the detachable needle tip 40a mentioned above. Elements 40, 44 and 42, 46 may be, for example, solid wire-like members or hollow (e.g., hypotubes). The wire-like or hypotube element 44 (coupled with two-piece needle 40) is fixed to the actuator 22a, while the wire or hypotube element 46 (coupled to the needle 42) is fixed to the actuator 22b. For purposes of deploying the needles 40, 42 in a distal direction, the actuators 22a, 22b are respectively pushed in a distal direction.

Further reference is made to FIGS. 3A, 3B, 4A, 4B, 5A, 5B, 6A, 6B, 7A, 7B, 8A, 8B and 9 which progressively illustrate additional structure and function or methodology of the device 10. While the pivotal element 24 is in the first deployed orientation as shown in FIG. 4B, suture needle 40 is deployed or moved in a distal direction by pushing the proximal actuator 22a in a distal direction as indicated by the arrow 43 (FIG. 4A) and against the bias provided by a coil spring 25. Other forms of biasing members may be used. The second needle or retrieval needle 42 is operated in a similar manner as will be shown and described. The initial step is shown in FIG. 4A by arrow 43 indicating movement of the needle 40 in a distal direction toward the coupling member 48 attached to the pivotal element 24. The pivotal element 24 has been actuated or deployed into its first deployed orientation intended to receive the detachable needle tip 40a. This is accomplished by rotating the lever 20 in a clockwise direction (see progression of FIGS. 3A and 4A). In this position, the lever 20 also blocks any movement of the actuator 22b, thereby preventing unintended deployment of the second needle 42. The respective positions of the lever 20 discussed herein may be held or temporarily locked in place by detents or other suitable structure. FIGS. 5A and 5B illustrate the state of the actuator 22a, spring 25 and needle 40 after rotation of the lever 20 and then pushing of the actuator 22a in a distal direction. Here, the respective needle tip 40a engages and connects with a first end of coupling member 48. The needle tip 40a is fixed to an elongate tensile member or suture 50, while needle 42 has an integral (i.e., fixed) tip 42a. The word "integral" here encompasses fully integral constructions as well as constructions in which the tip 42a is fixedly (i.e., not "removably") coupled to the remainder of the integral needle 42. As shown in FIGS. 6A and 6B, needle body 40b will be retracted slightly by the spring-biased proximal movement of actuator 22a, i.e., by way of the expansion of coil spring 25 when the actuator 22a is released. By way of reviewing the progression of FIGS. 6A and 6B to FIGS. 7A and 7B, it will be apparent that the next step is to rotate the lever 20 in a counter-clockwise direction to rotate the pivotal element 24 into its second deployed orientation, shown in FIG. 7B, intended to receive the needle tip 42a. The actuator 22b has been pushed distally against the force of a compression spring 27 such that the needle tip 42a engages and connects with a second end of coupling member 48. When the actuator 22b is released as indicated by the arrow in FIG. 7A, the expansion force of spring 27 pulls the needle 42, including tip 42a, proximally and carries with it the coupling member 48 and the attached needle tip 40a and tensile element or suture 50. This is shown in FIGS. 8A and 8B. The coupling member 48 is fixed to the pivotal element 24 with a "one-way" connection such that it may only move out from the pivotal element 24 in the direction shown in FIG. 8B. A proximal, rotatable portion 12a of the handle 12 is rotated as further shown in FIGS. 8A and 9 to expose an opening 29 allowing actuator 22b to be removed and for the needle 42, coupling member 48, needle tip 40a and tensile element or suture 50 to be withdrawn in a proximal direction as shown in FIG. 8B.

Figure 10:
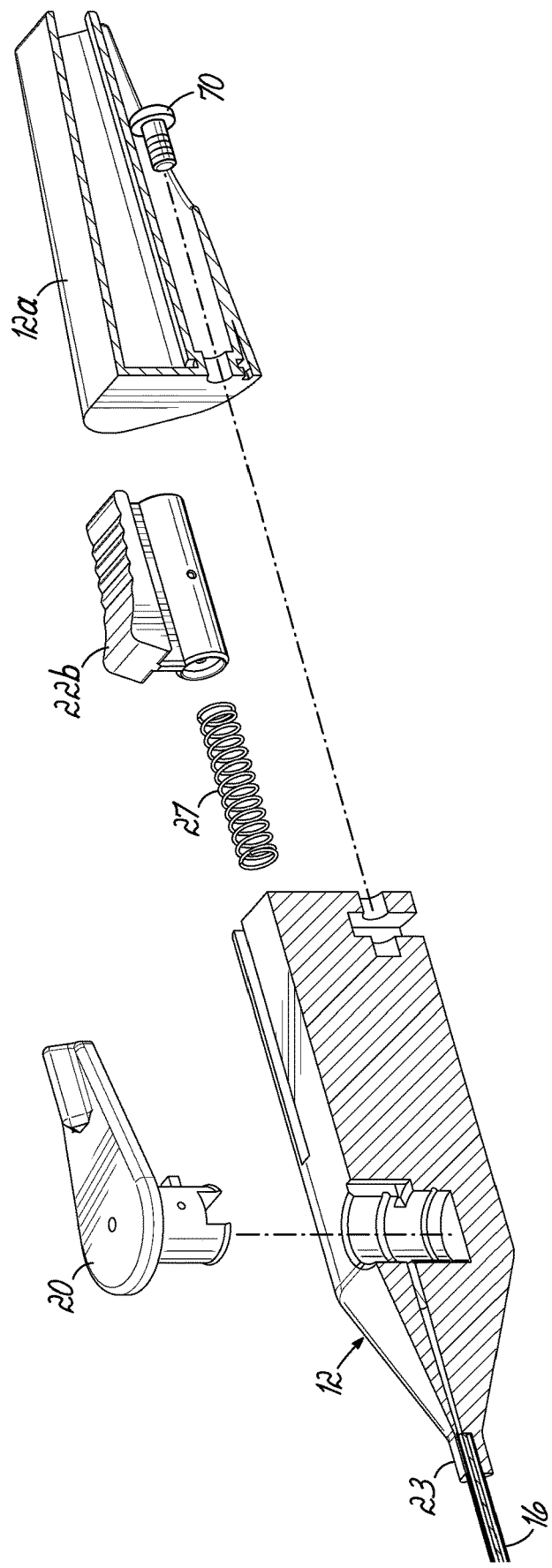
FIG. 10 is an exploded sectional view of the handle of the suturing device of FIGS. 1 and 2.

FIG. 10 is an exploded perspective view illustrating the handle 12, lever 20, actuator 22b, spring 27 and rotatable handle portion 12a held to the remaining portion of the handle 12 by a threaded fastener 70.

Figure 11A:
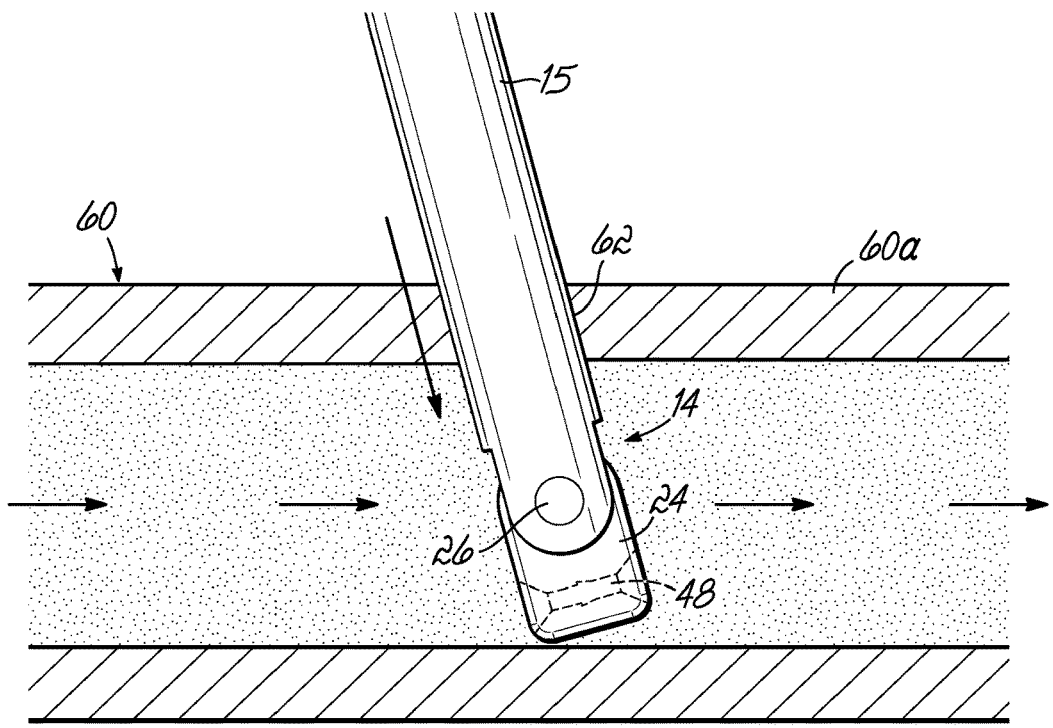
FIGS. 11A through 11J schematically illustrate the use of the suturing device of FIGS. 1 and 2, and particularly, the distal end and the suturing mechanism within a blood vessel.
Figure 11B:
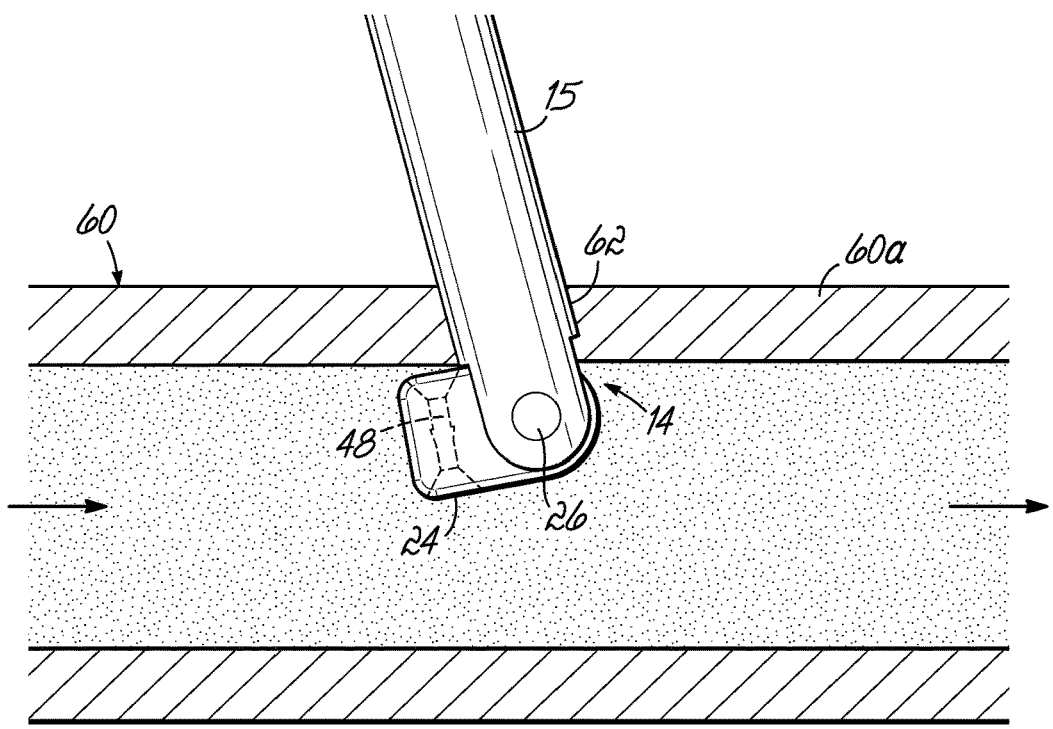
Figure 11C:
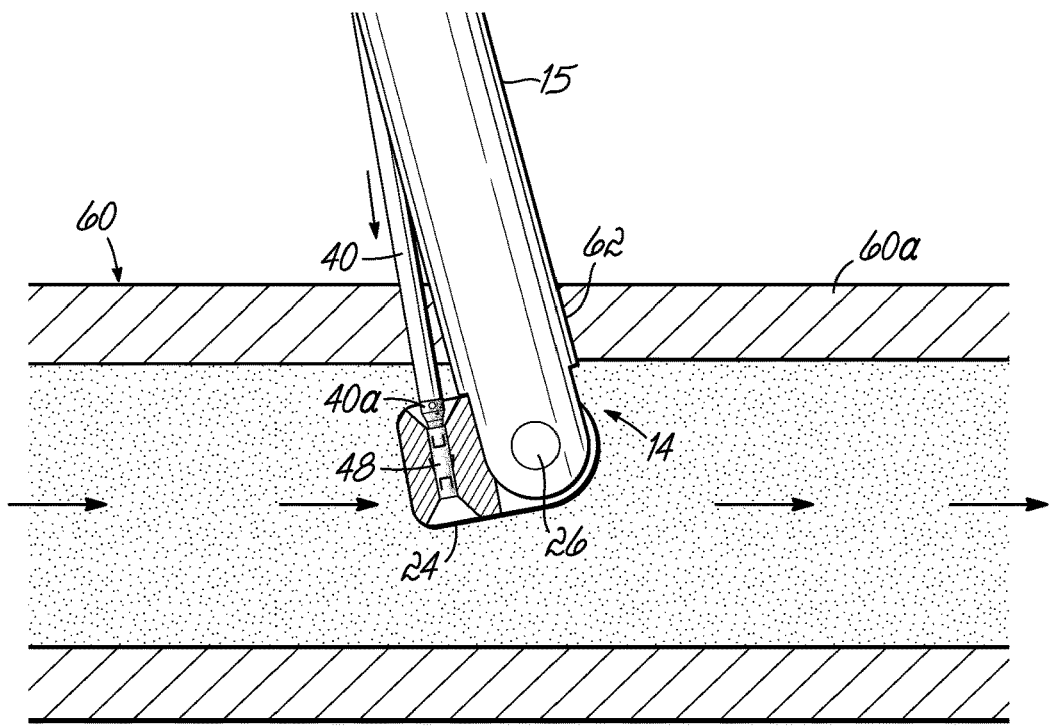
Figure 11D:
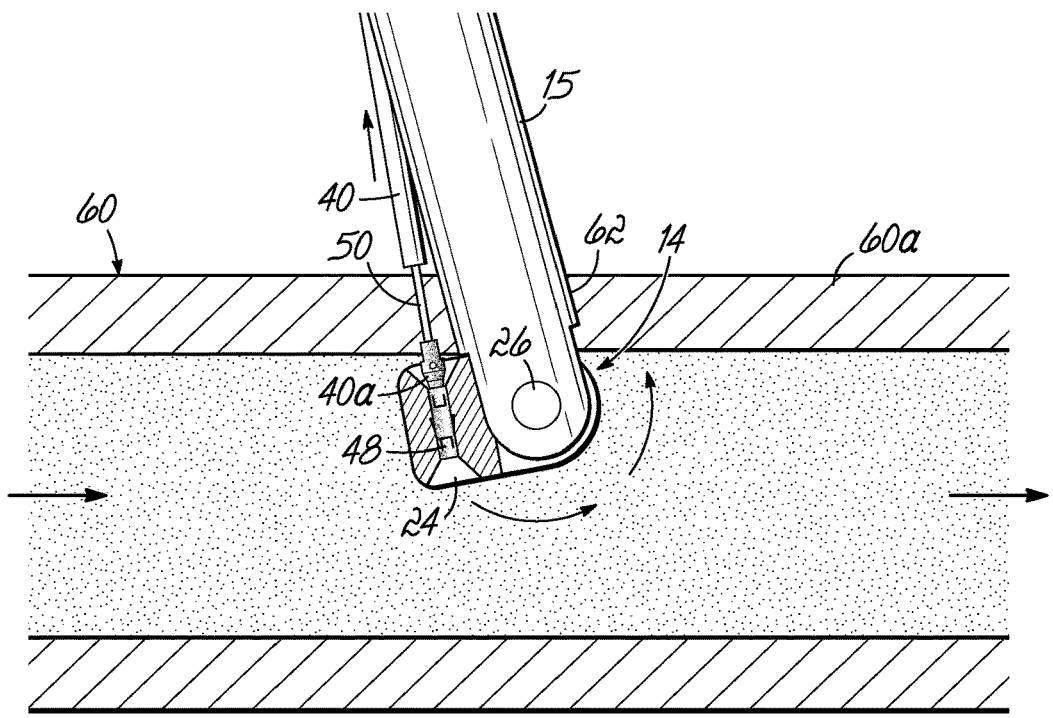
Figure 11E:
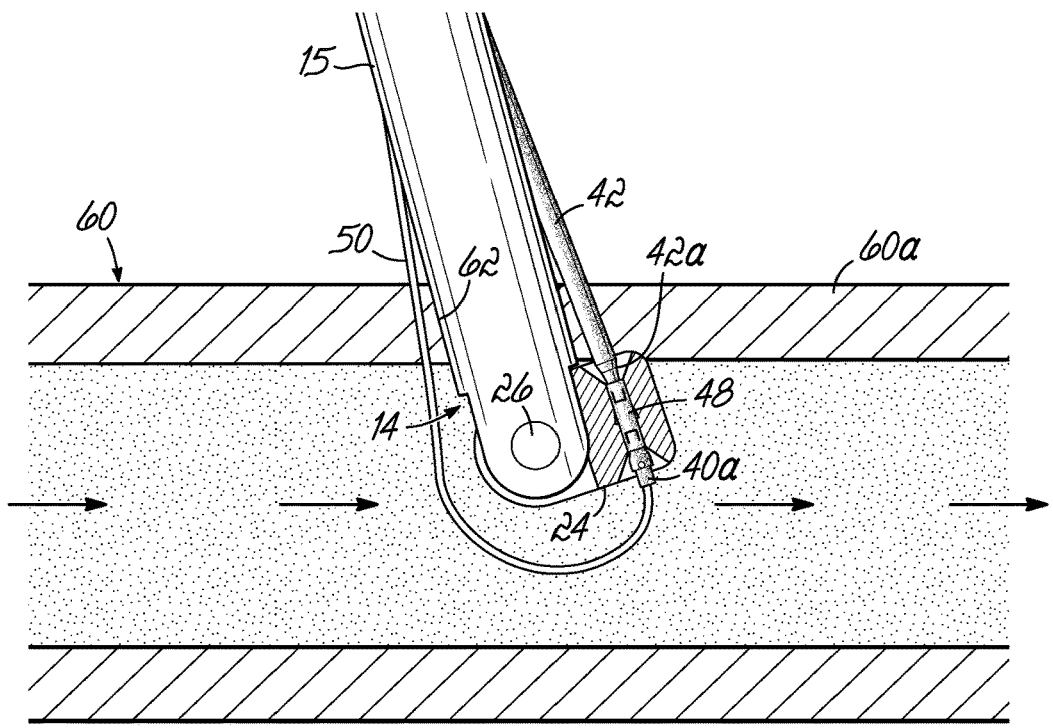
Figure 11F:
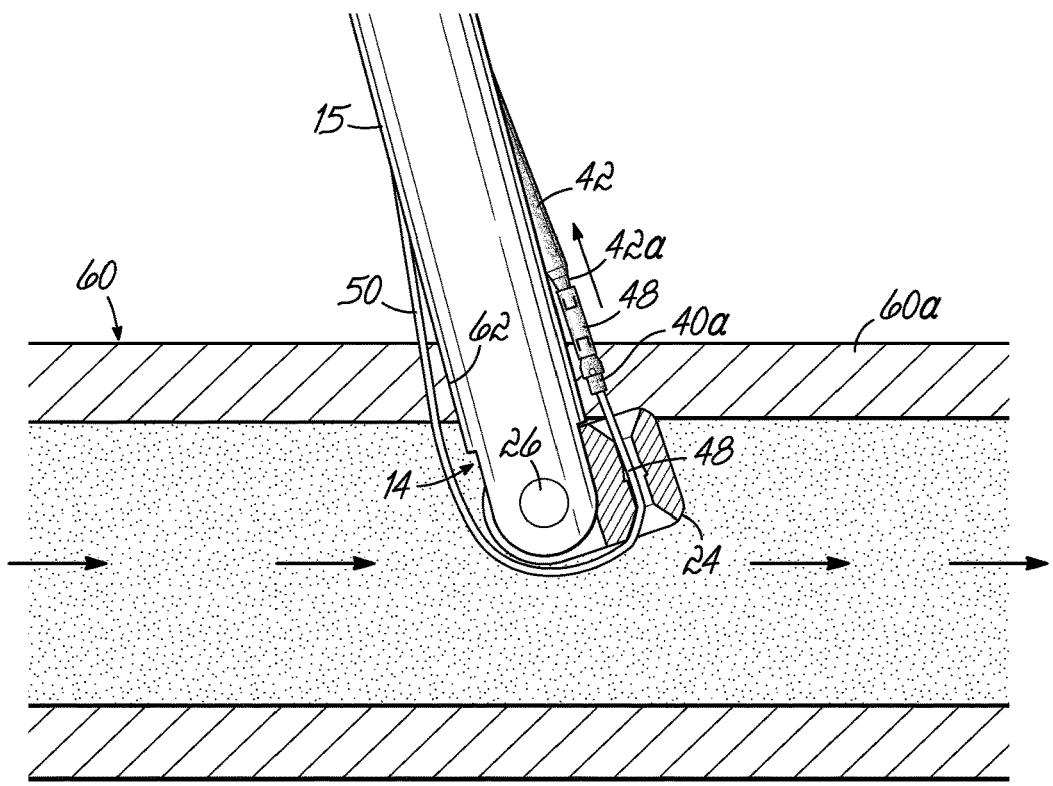
Figure 11G:
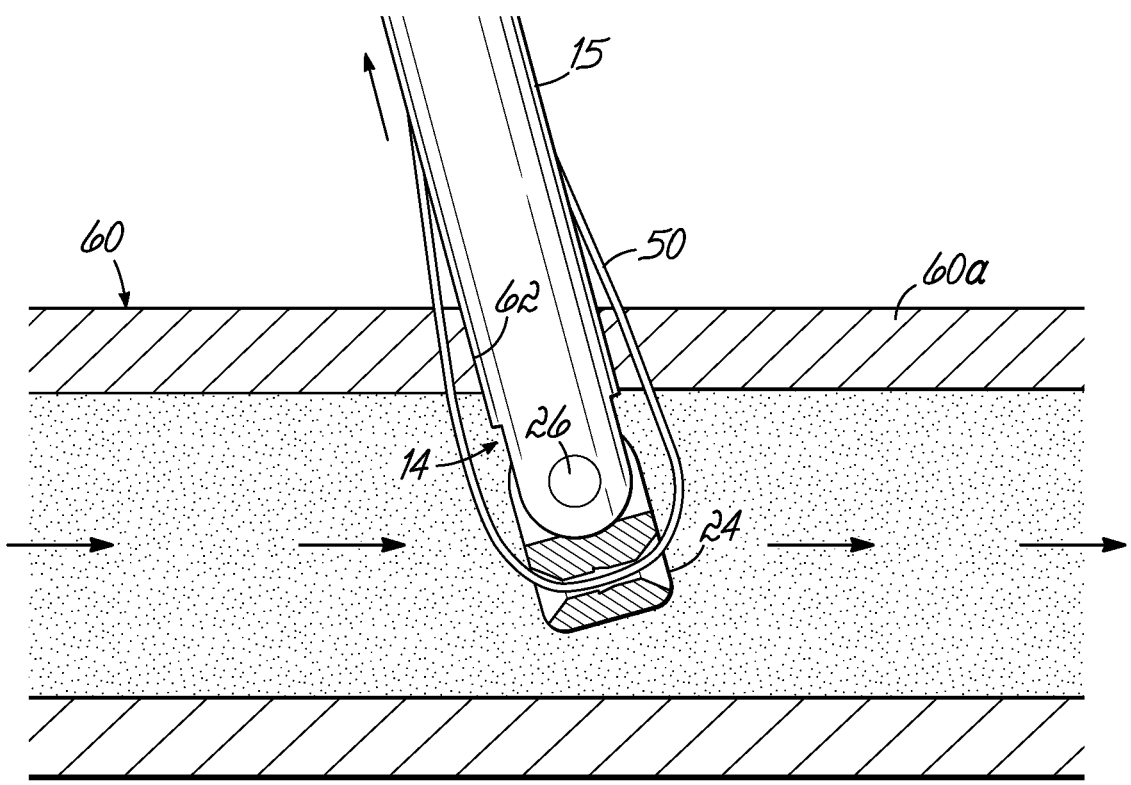
Figure 11H:
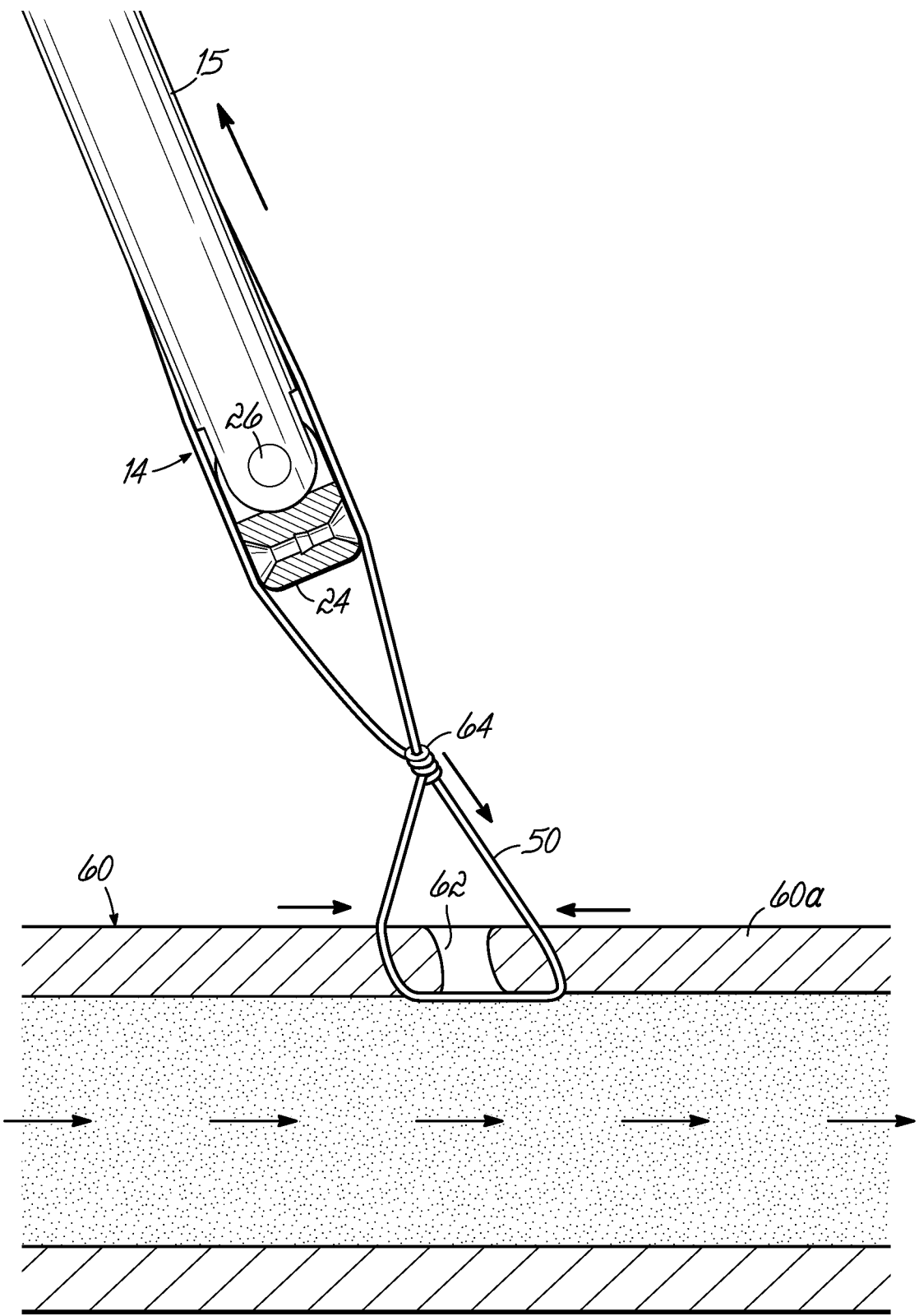
Figure 11I:
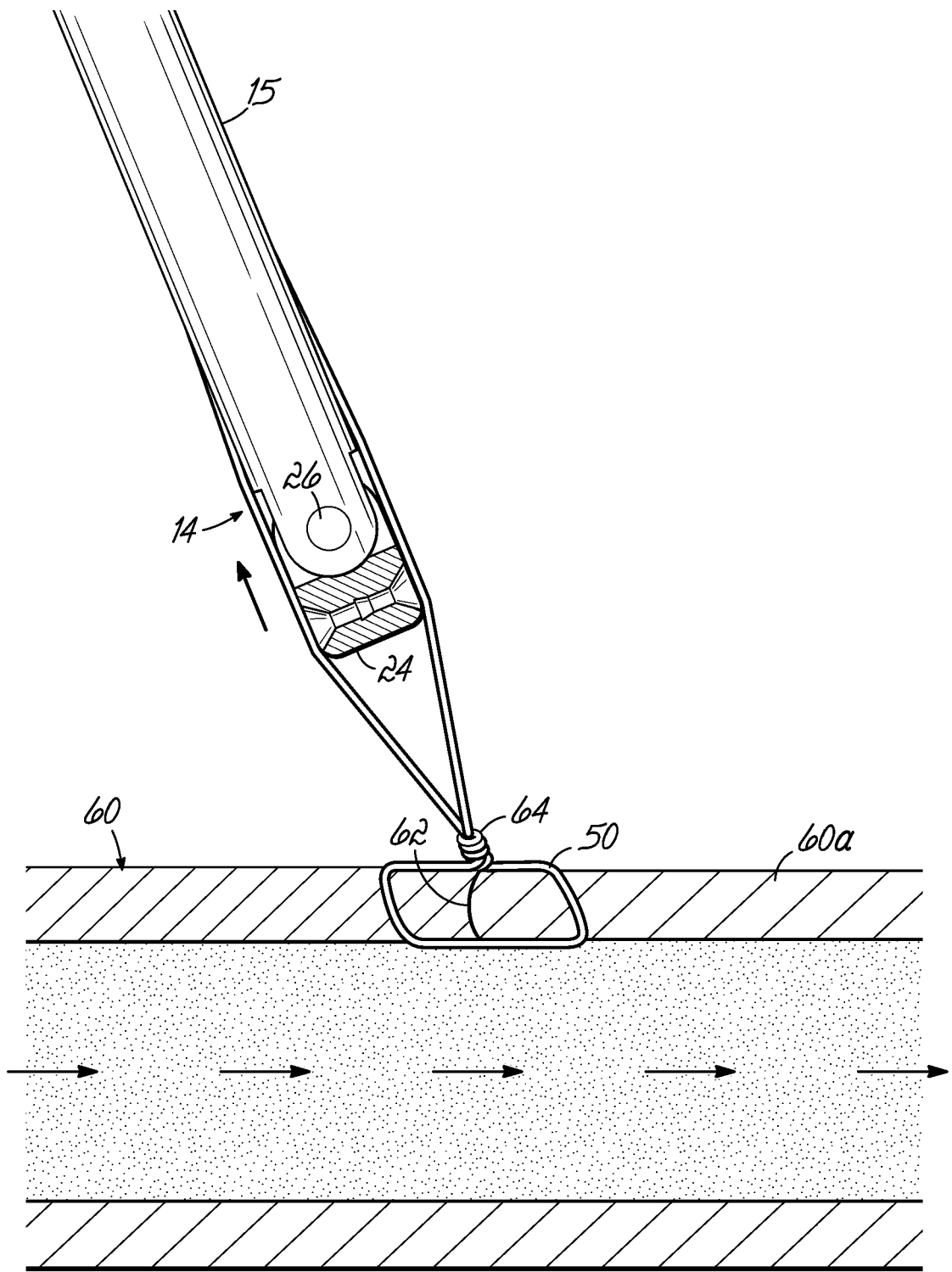
Figure 11J:
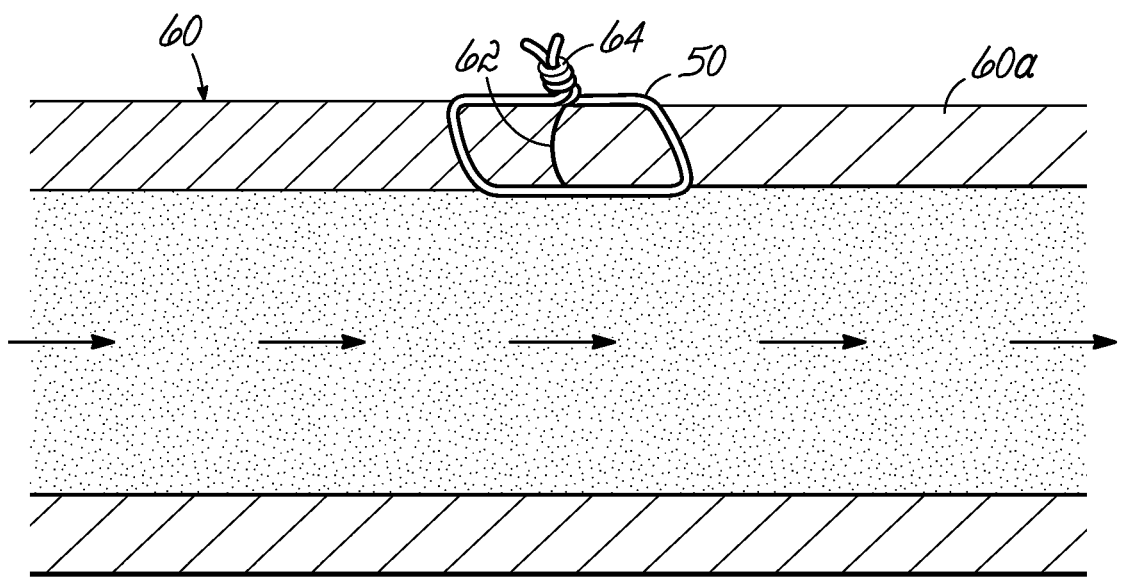

FIGS. 11A through 11J schematically illustrate the use of the device 10 and, particularly, the distal end and the suturing mechanism 14 within a blood vessel 60, such as the common carotid artery, for closing a puncture or opening 62 in a wall 60a of the blood vessel 60. The distal end of the needle guide 15, with the pivotal element 24 aligned with its lengthwise extent parallel to and in alignment with the lengthwise axis of the needle guide 15, is inserted into the sheath 18 (not shown). The suturing mechanism 14 is activated within the vessel 60 and the pivotal element 24 is pivoted into the angled orientation relative to the lengthwise axis of the needle guide 15, the first deployed orientation, as shown in FIG. 11B by rotating the lever 20 (FIG. 4A) as previously discussed. The pivotal element 24 is then pulled proximally against the interior of the vessel wall 60a by slightly pulling proximally on the device 10 and therefore the needle guide 15 as shown in FIG. 11B. Once the pivotal element 24 is in this position, needle 40 is deployed or moved distally as described. Specifically, actuator 22a (see FIGS. 4A, 4B and 5A, 5B) is pushed distally such that the needle tip 40a connects with a first end of the coupling member 48 as shown in FIG. 11C. Needle body 40b is retracted proximally by releasing actuator 22a as shown and described in connection with FIGS. 6A and 6B. This causes the needle tip 40a to detach from the needle body 40b while leaving the tensile element or suture 50 fixed to the needle tip 40a and the needle tip 40a still fixed to the coupling member 48. As illustrated in FIGS. 11D and 11E, the pivotal element 24 is then rotated approximately 190° into the second deployed orientation by pivoting or rotating the lever 20 counter-clockwise as described in connection with the progression of FIGS. 6A, 6B, 7A and 7B. Needle 42 is then moved distally, as described above, to connect the needle tip 42a with the second end of the coupling member 48. As further shown in FIG. 11F, the needle 42, coupling member 48, needle tip 40a and tensile element or suture 50 are pulled in a proximal direction through the vessel wall 60a. Pulling rearwardly or proximally on the integral needle 42 by further retracting or pulling on the actuator 22b (see FIGS. 8A, 8B and 9) will then pull both the coupling member 48 and the needle tip 40a and connected suture or tensile element 50 through the vessel wall 60a adjacent the puncture or opening 62. As shown in FIG. 11G, the pivotal element 24 is then actuated into its original aligned orientation as previously described for allowing the device 10 and, particularly, the distal end of the needle guide 15 and the suturing mechanism 14 to be pulled proximally and removed from the blood vessel 60. The aligned orientation of the pivotal element 24 shown in FIG. 11G is achieved by moving the lever 20 to its aligned or neutral position shown in FIG. 3A. As further shown in FIGS. 11H and 11I, a suture knot 64 is deployed from the needle guide 15, such as through the needle body 40 if it is hollow, or through a lumen in the needle guide 15. More preferably, the suture knot 64 may deploy from the other needle 42, with the "coils" of the knot 64 wrapped around the needle 42. Alternatively, the suture 50 and suture knot 64 may be located outside of the needle guide 15. The suture knot 64 may be any desired form of knot suitable for tying off a suture, such as the type that will automatically tighten as one end of the suture 50 is pulled. One form of knot suitable for use in this situation is the "Tennessee Slider" knot. The knot 64 is tightened against the outside of the vessel 60 as shown in FIG. 11J to fully approximate or close the opening 62.

FIGS. 14A and 14B illustrate how the device 10 is exchanged internally with the introducer sheath 18 while within the blood vessel 60. The device 10 is inserted into the blood vessel 60 prior to the removal of the introducer sheath 18. Depth markers or indicators on the outer surface of the device 10 can give visual feedback to the doctor as to how far to insert the device 10 into the introducer sheath 18. The pivotal element 24 is actuated into its angled, transverse orientation as previously described (FIG. 2B). The introducer sheath 18 and the device 10/shaft 16 are pulled proximally out of the vessel 60 until the angled pivotal element 24 contacts the inner wall surface 60a (best depicted in FIG. 11B). The introducer sheath 18 is then pulled rearward or proximally along the shaft 16 while the suturing mechanism 14 remains within the vessel 60. The introducer sheath 18 remains in surrounding relation to the shaft 16 for the remainder of the procedure. The device 10 is then ready for the deployment of the suture needles 40, 42 and the remainder of the procedure as described herein.

The shaft 16 may be a quad-lumen flexible catheter in which one of the lumens carries the actuator wire 30, two of the lumens respectively carry the needles 40, 42, and the fourth lumen may be used as a blood port for indicating to the doctor when the distal end of the device 10 has entered the vessel 60.

FIG. 12 illustrates an alternative deployment control handle 12' which may be used to practice the methods more fully discussed above. In this figure, reference numerals that are identical to those shown in prior figures identify the same structure and function referenced and described above. Therefore, additional description is not deemed necessary. Reference numerals that are identical to the those described in the first embodiment but include prime marks (') refer to components that are substantially similar to that described in the first embodiment but having differences that are described herein below, or are readily apparent. This alternative handle 12' includes an actuator in the form of a partially rotatable lever 20 which operates substantially as described above. The lever 20 is rotated to rotate the pivotal element 24 to a first position (see FIG. 11B). The user then moves the needle 40 distally to engage the pivotal element 24 (see FIG. 11C) by sliding a button 80 forward or distally after the lever 20 has been rotated to an actuated position (not shown). As in the first embodiment, a spring return mechanism (not shown) is coupled with the button 80 and needle 40. The needle 42 is moved distally by depressing a plunger 82, which is affixed to the needle 42, in a distal or forward direction (see FIG. 11E). As described in more detail above, this is done after the lever 20 has been rotated to pivot the element 24 to its second, transverse orientation (see FIG. 11E). The plunger 82 may also be coupled to a spring biased return mechanism (not shown) and may be fully removed in a proximal direction to remove the needle 42 and suture 50 as previously described (see FIG. 9). The remainder of the procedure may be the same as described above in reference to the first embodiment.

FIG. 13 illustrates an alternative deployment control handle 12" which may be used to practice the methods more fully discussed above. In this figure, reference numerals that are identical to those shown in prior figures identify the same structure and function referenced and described above. Therefore, additional description is not deemed necessary. Reference numerals that are identical to the those described in the first embodiment but include double prime marks (") refer to components that are substantially similar to that described in a previously described embodiment but having differences that are described herein below, or are readily apparent. This alternative handle 12" includes an actuator in the form of a slide button 90. The user moves the slide button 90 forward or distally to rotate the pivotal element 24 to a first position (see FIG. 11B). The user then moves the needle 40 distally to engage the pivotal element 24 (see FIG. 11C) by sliding a button 80 forward or distally after the button 90 has been moved forward or distally to its first actuated position (not shown). As in the first embodiment, a spring return mechanism (not shown) is coupled with the button 80 and needle 40. The needle 42 is moved distally by depressing the plunger 82, which is affixed to the needle 42, in a distal or forward direction. This is done after the user moves the slide button 90 rearwardly or proximally to pivot the element 24 to its second, transverse orientation (see FIG. 11E). The plunger 82 may also be coupled to a spring biased return mechanism (not shown) and may be fully removed in a proximal direction to remove the needle 42 and suture 50 as previously described. The remainder of the procedure may be the same as described above in reference to the first embodiment.

FIGS. 14A and 14B illustrate how the device 10 is exchanged internally with the introducer sheath 18 while within the blood vessel 60. The device 10 is inserted into the blood vessel 60 prior to the removal of the introducer sheath 18. Depth markers or indicators on the outer surface of the device 10 can give visual feedback to the doctor as to how far to insert the device 10 into the introducer sheath 18. The pivotal element 24 is actuated into its angled, transverse orientation as previously described (FIG. 14B). The introducer sheath 18 and the device 10/shaft 16 are pulled proximally out of the vessel 60 until the angled pivotal element 24 contacts the inner wall surface 60*a* (best depicted in FIG. 11B). The introducer sheath 18 is then pulled rearward or proximally along the shaft 16 while the suturing mechanism 14 remains within the vessel 60. The introducer sheath 18 remains in surrounding relation to the shaft 16 for the remainder of the procedure. The device 10 is then ready for the deployment of the suture needles 40, 42 and the remainder of the procedure as described herein.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination within and between the various embodiments. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A vessel closure device, comprising:
   a proximal end including a handle with a needle actuator and a suturing mechanism actuator;
   an elongate shaft coupled to the handle;
   a suturing mechanism coupled to a distal end of the elongate shaft, and including a pivotal element coupled to the suturing mechanism actuator;
   first and second needles associated with the suturing mechanism; and
   a tensile member coupled to the first needle;
   wherein at least one of the first and second needles is coupled to the needle actuator;
   wherein the pivotal element is configured to pull the tensile member and is configured to be moved by the suturing mechanism actuator between an insertion and removal orientation, a first deployed orientation aligned with the first needle, and a second deployed orientation aligned with the second needle;
   wherein the suturing mechanism is configured to be activated within a vessel through an opening in a wall of the vessel,
   wherein the first and second needles are configured to be directed through the vessel wall adjacent to the opening,
   wherein at least one of the first and second needles is configured to be directed through the vessel wall with the needle actuator, and
   wherein the tensile member is configured to be pulled through the vessel wall adjacent to the opening to close and seal the opening.

2. The vessel closure device of claim 1, wherein the suturing mechanism further comprises a coupling member having first and second ends, the first end is configured to be coupled to the first needle and the second end is configured to be coupled to the second needle, and the coupling member is configured to pull the tensile member through the vessel wall.

3. The vessel closure device of claim 2, wherein the first needle includes a detachable tip coupled to the tensile member, and the detachable tip is configured to be coupled to the first end of the coupling member.

4. The vessel closure device of claim 2, wherein the coupling member comprises a flexible coupling member.

5. The vessel closure device of claim 1, wherein the needle actuator is spring-biased into a position for retracting at least one of the first and second needles.

6. The vessel closure device of claim 1, wherein the needle actuator is a first needle actuator, and the vessel closure device further comprises a second needle actuator,
   wherein the first needle is coupled to the first needle actuator,
   the first needle is configured to be directed through the vessel wall with the first needle actuator, the second needle is coupled to the second needle actuator, and
   the second needle is configured to be directed through the vessel wall with the second needle actuator.

7. The vessel closure device of claim 6, wherein the second needle actuator is spring-biased into a position for retracting the second needle.

8. The vessel closure device of claim 1, further comprising a flexible strain relief coupled between the handle and the elongate shaft.

9. The vessel closure device of claim 1, further comprising an introducer sheath through which the suturing mechanism is configured to be directed into a blood vessel wherein the introducer sheath can then be withdrawn from the blood vessel with the suturing mechanism remaining in the blood vessel thereby inhibiting blood from exiting the blood vessel through the opening.

10. The vessel closure device of claim 1, wherein at least one of the first and second deployed orientations is an angled orientation.

11. The vessel closure device of claim 1, wherein the pivotal element extends in generally opposite directions in the first and the second deployed orientations.

12. The vessel closure device of claim 1, further comprising a suture knot disposed on the tensile member.

13. The vessel closure device of claim 12, wherein the suture knot is configured to automatically tighten as at least one end of the tensile member is pulled.

14. The vessel closure device of claim 12, wherein the suture knot is a "Tennessee Slider" knot.

15. The vessel closure device of claim 1, wherein the pivotal element is configured to rotate 190° from the first deployed orientation to the second deployed orientation.

16. The vessel closure device of claim 1, wherein the tensile member is wrapped around at least one of the first and second needles.

17. The vessel closure device of claim 1, wherein the tensile member is wrapped around the elongate shaft, wherein the tensile member is wrapped around the shaft.

18. A vessel closure device, comprising:
    a proximal end including a handle with a first needle actuator, a second needle actuator, and a suturing mechanism actuator;
    an elongate shaft coupled to the handle;
    a suturing mechanism coupled to a distal end of the elongate shaft, and including a pivotal element coupled to the suturing mechanism actuator;
    a first needle associated with the suturing mechanism and coupled to the first needle actuator;
    a tensile member coupled to the first needle; and
    a second needle associated with the suturing mechanism and coupled to the second needle actuator;
    wherein the pivotal element is configured to pull the tensile member and is configured to be moved by the suturing mechanism actuator between an insertion and removal orientation, a first deployed orientation aligned with the first needle, and a second deployed orientation aligned with the second needle;

wherein the suturing mechanism is configured to be deployed within a vessel through an opening in a wall of the vessel while the pivotal element is in the insertion and removal orientation;

wherein the first needle is configured to be directed through the vessel wall adjacent to the opening to direct the tensile member adjacent to the opening using the first needle actuator while the pivotal element is in the first deployed orientation;

wherein the second needle is configured to be directed through the vessel wall adjacent to the opening to direct the tensile member adjacent to the opening using the second needle actuator while the pivotal element is in the second deployed orientation; and wherein the tensile member is configured to be pulled through the vessel wall adjacent to the opening to close and seal the opening.

19. The vessel closure device of claim 18, wherein the suturing mechanism further comprises a coupling member having first and second ends, the first end configured to be coupled to the first needle and the second end configured to be coupled to the second needle, and the coupling member is configured to pull the tensile member through the vessel wall.

20. The vessel closure device of claim 19, wherein the first needle includes a needle body and a detachable tip coupled to the tensile member, and the detachable tip is configured to be coupled to the first end of the coupling member.

21. The vessel closure device of claim 19, wherein the coupling member comprises a flexible coupling member.

22. The vessel closure device of claim 18, further comprising a flexible strain relief coupled between the handle and the elongate shaft.

23. The vessel closure device of claim 18, wherein the first needle actuator is spring-biased into a position for retracting the first needle.

24. The vessel closure device of claim 18, wherein the second needle actuator is spring-biased into a position for retracting the second needle.

25. The vessel closure device of claim 18, further comprising an introducer sheath through which the suturing mechanism is configured to be directed into a blood vessel wherein the introducer sheath can then be withdrawn from the blood vessel with the suturing mechanism remaining in the blood vessel thereby inhibiting blood from exiting the blood vessel through the opening.

26. The vessel closure device of claim 18, wherein at least one of the first and second deployed orientations is an angled orientation.

27. The vessel closure device of claim 18, wherein the pivotal element extends in generally opposite directions in the first and the second deployed orientations.

28. The vessel closure device of claim 18, further comprising a suture knot disposed on the tensile member.

29. The vessel closure device of claim 28, wherein the suture knot is configured to automatically tighten as at least one end of the tensile member is pulled.

30. The vessel closure device of claim 28, wherein the suture knot is a "Tennessee Slider" knot.

31. The vessel closure device of claim 18, wherein the tensile member is wrapped around at least one of the first and second needles.

32. The vessel closure device of claim 18, wherein the pivotal element is configured to rotate 190° from the first deployed orientation to the second deployed orientation.

33. The vessel closure device of claim 18, wherein the tensile member is wrapped around the elongate shaft.

\* \* \* \* \*